United States Patent
Rosenblatt

(10) Patent No.: US 10,993,794 B2
(45) Date of Patent: *May 4, 2021

(54) DEVICE AND METHOD OF PERFORMING CERCLAGE SACROCERVICOPEXY

(71) Applicant: Gynapex Surgical, LLC, West Newton, MA (US)

(72) Inventor: Peter L. Rosenblatt, West Newton, MA (US)

(73) Assignee: Gynapex Surgical, LLC, West Newton, MA (US)

( * ) Notice: Subject to any disclaimer, the term of this patent is extended or adjusted under 35 U.S.C. 154(b) by 141 days.

This patent is subject to a terminal disclaimer.

(21) Appl. No.: 16/251,988

(22) Filed: Jan. 18, 2019

(65) Prior Publication Data

US 2019/0151065 A1    May 23, 2019

Related U.S. Application Data

(63) Continuation-in-part of application No. 15/697,089, filed on Sep. 6, 2017, now Pat. No. 10,898,308, which (Continued)

(51) Int. Cl.
*A61F 2/00* (2006.01)
*A61B 17/04* (2006.01)
*A61B 17/06* (2006.01)

(52) U.S. Cl.
CPC ........ *A61F 2/0045* (2013.01); *A61B 17/0482* (2013.01); *A61B 17/06066* (2013.01); *A61B 17/06109* (2013.01); *A61B 2017/06019* (2013.01); *A61B 2017/06042* (2013.01); *A61B 2017/06052* (2013.01); *A61B 2017/06176* (2013.01); *A61F 2002/0072* (2013.01);

(Continued)

(58) Field of Classification Search
CPC ........ A61F 2/0045; A61F 5/005; A61B 17/06; A61B 17/0482
USPC .......................................................... 600/37
See application file for complete search history.

(56) References Cited

U.S. PATENT DOCUMENTS 7,131,943 B2   11/2006  Kammerer
2006/0122457 A1   6/2006  Kovac et al.
(Continued)

FOREIGN PATENT DOCUMENTS

RU         2538796 C2    1/2015
WO    WO-2010/138894 A2   12/2010

OTHER PUBLICATIONS

International Search Report and Written Opinion for International Application No. PCT/US2020/014069 dated May 14, 2020.
(Continued)

*Primary Examiner* — John P Lacyk
(74) *Attorney, Agent, or Firm* — Foley Hoag LLP; Rajesh Vallabh

(57) ABSTRACT

An implantable cerclage sacrocolpopexy medical device includes an elongate strip of flat, flexible material extending longitudinally from a first end to an opposite second end; a surgical needle attached to the first end of the elongate strip; and a loop at either the first end or the second end of the elongate strip. The medical device is positioned circumferentially around the cervix. The end of the elongate strip opposite the end having the loop is passed through the loop and attached to the sacrum or sacrospinous ligament.

18 Claims, 31 Drawing Sheets

Related U.S. Application Data is a continuation of application No. PCT/US2016/021214, filed on Mar. 7, 2016.

(60) Provisional application No. 62/709,591, filed on Jan. 23, 2018, provisional application No. 62/177,057, filed on Mar. 6, 2015.

(52) U.S. Cl.
CPC ............. *A61F 2220/0025* (2013.01); *A61F 2220/0075* (2013.01); *A61F 2220/0083* (2013.01)

(56) References Cited

U.S. PATENT DOCUMENTS

| | | |
|---|---|---|
| 2008/0021265 A1 | 1/2008 | Garbin et al. |
| 2008/0177132 A1 | 7/2008 | Alinsod et al. |
| 2009/0192346 A1 | 7/2009 | Rosenblatt |
| 2010/0305394 A1 | 12/2010 | Rosenblatt |

OTHER PUBLICATIONS

Lee, "Robotic Single-Site® Sacrocolpopexy: First Report and Technique Using the Single-Site® Wristed Needle Driver," Yonsei Medical Journal, 54(4):1029-1033 (2016).

DEVICE AND METHOD OF PERFORMING CERCLAGE SACROCERVICOPEXY

CROSS REFERENCE TO RELATED APPLICATIONS

This application claims priority from U.S. Provisional Patent Application No. 62/709,591 filed on Jan. 23, 2018. This application is also a continuation-in-part of U.S. patent application Ser. No. 15/697,089 filed Sep. 6, 2017, which in turn is a continuation of International Patent Application No. PCT/US2016/021214 filed Mar. 7, 2016, which claims the benefit of U.S. provisional application Ser. No. 62/177,057 filed Mar. 6, 2015. The entirety of each of the above-identified applications is hereby incorporated herein by reference.

FIELD

The disclosed subject matter relates to a system for treating pelvic disorders. Particularly, the present disclosed subject matter is directed towards a device and method of performing cerclage sacrocervicopexy.

BACKGROUND

A variety of methods and systems are known for treating vaginal prolapse, with sacrocolpopexy being considered by many surgeons to be the most advantageous treatment of vaginal vault prolapse. Sacrocolpopexy involves suspension of the vagina to the sacrum using an intervening graft material. There are several variations of the procedure, depending on the patient's anatomy and previous or concomitant surgery. For example, if the primary problem is uterine prolapse, the surgeon may choose to perform a sacrohysteropexy (attaching the upper posterior vagina and cervix to the sacral promontory. When combined or following supracervical hysterectomy, sacrocervicopexy is performed, which usually implies use of a "Y"-shaped mesh (similar to sacrocolpopexy), which covers the cervix and extends over the anterior and posterior vaginal fascia.

In the past, sacrocolpopexy was typically performed through an abdominal incision, although more recently, laparoscopic and robotic sacrocolpopexy techniques have been utilized by pelvic reconstructive surgeons to reduce the morbidity associated with laparotomy. Various materials have been used in this procedure, including both natural and synthetic materials, although permanent synthetic mesh is most often described, due to excellent long-term results described in the literature. Of the synthetic materials in use today, the most commonly used is type I, macroporous, monofilament, lightweight polypropylene. This material is well tolerated, easy to handle, and resistant to infection and erosion through tissues in the pelvis, especially the vagina.

Most surgeons who perform sacrocolpopexy employ a "Y-shaped" configuration of the mesh. This configuration includes two extensions of the mesh that provide coverage to the posterior and anterior vaginal walls. During the surgery, the bladder is advanced off the anterior vagina and the rectum is dissected free of the posterior vagina by entrance into the rectovaginal septum. The mesh extensions are then placed over the anterior and posterior vagina and sutured in place with multiple interrupted sutures or, more recently, continuous barbed suture. Once the vaginal sutures have been placed, the surgeon attaches the mesh to the anterior longitudinal ligament of the sacrum, either at the promontory or lower, in the hollow of the sacrum. Although traditional suturing of the mesh to the sacrum is commonly used, other surgeons use a tacking device to fix the mesh to the sacrum. Finally, some surgeons choose to bury the mesh under the peritoneum, to prevent the potential development of internal intestinal hernia and subsequent obstruction.

Support of the apex of the vagina (which may be the cervix in women who have not had hysterectomy) is an important part of most prolapse operations and that apical support resolves many cystoceles and rectoceles. Apical support can be assessed in the office setting or in the operating room, by gently supporting the cervix with an instrument, such as a tenaculum or scopettes. In this manner, the anterior and posterior vaginal walls can be evaluated to determine whether additional repair to these compartments is required at the time of reconstructive surgery. In many instances, support of the cervix alone reduces prolapse of the anterior and/or posterior compartments. In those cases, it may be appropriate to only address cervical support at the time of surgery.

Cervical cerclage refers to one of several surgical procedures in which a material, such as mesh, tape or suture is used to reinforce the cervix. This is most often performed for women with a history of an incompetent cervix associated with a mid-trimester pregnancy loss. Typically, a pregnant woman with an incompetent cervix will have experienced painless dilation of the cervix, resulting in a pregnancy loss. The cerclage is typically performed after 12 weeks gestation in a subsequent pregnancy, after confirming fetal viability. The two most common techniques used are the McDonald and the Shirodkar techniques. Whereas the McDonald technique does not require any surgical dissection, the Shirodkar procedure involves an anterior and posterior incision, in order to advance the bladder and rectum, respectively, off the cervix. With the Shirodkar technique, the cerclage material may be completely buried under the vaginal epithelium once the anterior and posterior incisions are closed at the completion of the procedure. Placement of the cerclage material is performed in several tissue bites, staying medial to the uterine vessels, which are located bilaterally at the 3:00 and 9:00 positions. Once the material has been placed circumferentially, the two ends of the material are usually tied together, either anteriorly or posteriorly, and the knot may be placed either under the epithelium or within the vaginal canal, to facilitate removal of the cerclage. The cerclage may be removed late in the pregnancy, although if a cesarean section is planned, the cerclage may be left in place, and even used for a subsequent pregnancy.

Many surgeons find that laparoscopic suturing and knot tying are the most time consuming and challenging aspects of sacrocolpopexy and its variants. Furthermore, extensive dissection of the bladder and rectum off the cervix and upper vagina can be difficult for the laparoscopic or open surgeon, especially in the patient who has previously undergone surgery in that area (e.g. cesarean section).

There thus remains a need for an effective and efficient method and system for performing pelvic disorders with a device(s) that simplify sacrocolpopexy procedures in order to expand the usage of this proven operation for pelvic organ prolapse.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a device for and method of treating pelvic disorders, including pelvic organ prolapse.

An exemplary implantable cerclage sacrocolpopexy medical device in accordance with one or more embodiments comprises an elongate strip of flat, flexible material extending longitudinally from a first end to an opposite second end; a surgical needle attached to the first end of the elongate strip; and a loop at either: (1) the first end of the elongate strip proximate the needle, wherein the loop is sized and shaped to enable passage therethrough of the second end of the elongate strip after the elongate strip has been positioned to encircle the cervix in a cerclage configuration and the needle has been detached from the elongate strip, and wherein the second end of the elongate strip is configured for attachment to the sacrum, or (2) the second end of the elongate strip, wherein the loop is sized and shaped to enable passage therethrough of the first end of the elongate strip after the elongate strip has been positioned to encircle the cervix in a cerclage configuration and the needle has been detached from the elongate strip, and wherein the first end of the elongate strip is configured for attachment to the sacrum.

A exemplary method of treating prolapse in a patient in accordance with one or more embodiments comprises: (a) positioning an implantable cerclage sacrocolpopexy medical device circumferentially around the cervix of the patient, said medical device comprising an elongate strip of flat, flexible material extending longitudinally from a first end to an opposite second end, a surgical needle attached to the first end of the elongate strip, and a loop at either the first end or the second end; (b) detaching the surgical needle from the medical device and removing the surgical needle from the operative field; (c) passing the end of the elongate strip opposite the end having the loop through the loop; and (d) attaching the end of the elongate strip passed through the loop to the sacrum of the patient.

Devices in accordance with various embodiments include a mesh segment with a single needle on one end (either straight or curved, and either sharp or blunt-tipped) and some form of loop on the other end (or the same end, as will be described). Once the needle is placed circumferentially around the cervix (after dissecting the bladder, and potentially the rectum, off the cervix), the needle is detached and removed from the operative field. One end of the mesh strip is then passed through the loop on the other end of the mesh strip (which has been placed posterior to the cervix) and is then brought up to the desired location on the anterior ligament of the sacrum and attached with some fixation technique (e.g., suture or surgical tacks) after determining the proper tension on the mesh.

Devices in accordance with various embodiments can be used either totally "from above" (laparoscopically, robotically, or through an abdominal incision) or in a combination of a vaginal approach (for performance of the cerclage) with an endoscopic or open approach for attachment of the mesh to the anterior longitudinal ligament of the sacrum. For example, following laparoscopic dissection from the sacrum to the cul-de-sac, the surgeon may change positions to a vaginal approach. A vaginal incision is made at the anterior cervico-vaginal junction and the bladder is advanced off the anterior portion of the cervix. A posterior vaginal incision is then made and the posterior cul-de-sac is entered. The cerclage is then performed and the sacral tail is placed intraperitoneally for subsequent attachment to the sacrum. The anterior and posterior vaginal incisions are then closed with absorbable suture.

Alternatively, the entire procedure may be performed laparoscopically or robotically with the same devices described below. After dissection from the sacrum to the cul-de-sac, the anterior peritoneum is opened and a bladder flap is created, exposing the anterior cervix. The cerclage is then performed endoscopically, starting posterior to anterior on one side and then anterior to posterior on the contralateral side. The needle may be placed either medial or lateral to the uterine vessels.

It should be understood that whereas each of the figures shows a particular shaped needle, the needle on each of these embodiments may be curved, straight, or "ski" configuration, and may be either tapered or blunt-tipped. In addition, in any of these configurations, a plastic sheath may cover the area of the mesh or suture that is connected to the swaged needle. This may facilitate passage of the mesh material through the cervical tissue.

In some embodiments, one end of the mesh strip is swaged to a straight or curved needle, which is either sharp or blunt-tipped.

In some embodiments, the end of the mesh strip that is swaged on to a needle has a plastic sleeve covering the area where the mesh is swaged on to the needle, in order to provide less resistance as the mesh is brought through the cervical tissue.

In some embodiments, the needle is swaged on to a suture loop attached to the end of the mesh strip. The suture loop may also pass through an eyelet on the needle. On the same end of the mesh, there is a second, smaller suture loop, which is either threaded through the end of the mesh strip, or ultrasonically welded, or attached to the mesh strip end with another method of fixation. It is through this second, smaller loop that the other end of the mesh strip is threaded through before it is brought up to the desired location on the anterior ligament of the sacrum.

In some embodiments, the other end of the mesh strip (the non-needle end of the strip) has either a loop of permanent suture attached (either threaded through the mesh pores, ultrasonically welded to the mesh, or some other attachment method), or a folded over end of the mesh to create a loop, through which the other end of the mesh is threaded and then brought up to the sacrum for attachment.

It should be noted that the non-loop end of the mesh in any of the embodiments may be wider than the end of the mesh that has the loop. Therefore, the end of the mesh that will encircle the cervix may be more narrow and the end of the mesh that will extend and attach to the sacrum may be wider.

In an exemplary embodiment the medical device comprises a base portion comprising a flexible, flat material and having a length extending from proximal end and a distal end, and a width extending from a first side to a laterally opposed second side; at least one arm extending from at least one of the first or second sides, the at least one arm extending a distance greater than the width of the base portion; wherein the at least one arm is sized and shaped to be secured around at least a portion of a cervical isthmus.

The flexible, flat material may be mesh, or other flat, flexible materials, such as fabric, cross-linked or non-cross-linked biologic grafts, or combinations thereof. Throughout this disclosure, where reference is made in this disclosure to "mesh," it is to be understood that other flat, flexible materials may be used. For example, each of the various portions of the devices described herein, such as the base portion, sacral portion, anterior portion, posterior portion, and arm, may be made of mesh or other flat flexible materials.

Additionally or alternatively, in some embodiments the medical device comprises a flexible, flat base portion with a length extending longitudinally from a proximal end to a distal end, and width extending from a first side to a laterally opposed second side; at least one arm extending from at least one of the first or second sides; and wherein the at least one arm extends a distance greater than the width of the base portion.

In some embodiments the at least one arm is integrally formed with the base portion. In some embodiments the at least one arm extends from the first side and the base portion includes an aperture disposed proximate the second side.

In some embodiments the aperture is sized and shaped to receive the at least one arm irreversibly.

In some embodiments the medical device further comprises a needle disposed at the distal end of the at least one arm.

In some embodiments the medical device further comprises a locking mechanism, the locking mechanism having an opening to receive a portion of the at least one arm.

In some embodiments the base portion is formed from woven fixed-length fibers, and the at least one arm is formed from an elastic material.

In some embodiments the at least one arm is configured as a suture.

In some embodiments the at least one arm includes a plurality of retention features projecting outward from the at least one arm.

In some embodiments the at least one arm comprises a first arm extending from the first side of the base portion, and a second arm extending from the second side of the base portion.

In some embodiments the medical device further comprises a connector disposed at the distal end of the at least one arm, the connector having an opening to engage a needle.

In some embodiments an implantable sacrocolpopexy medical device comprises: a sacral portion having a length extending from a proximal boundary to a distal boundary, and a width extending from a first side to a laterally opposed second side; an anterior portion having a length extending from a proximal boundary to a distal boundary, and a width extending from a first side to a laterally opposed second side; a posterior portion having a length extending from a proximal boundary to a distal boundary, and a width extending from a first side to a laterally opposed second side; a first arm extending from the first side of the posterior portion, the first arm extending a distance greater than the width of the posterior portion; and a second arm extending from the second side of the posterior portion, the second arm extending a distance greater than the width of the posterior portion.

In some embodiments the anterior portion includes a first eyelet disposed proximate the first side and a second eyelet disposed proximate the second side.

In some embodiments the at least one eyelet includes a base having at least one slot formed therein.

In some embodiments the base includes a plurality of projections extending outward from the base surface.

In some embodiments the anterior portion is formed as a separate component from the posterior portion.

In some embodiments the at least one of the first and second arms includes a needle.

In some embodiments the medical device further comprises a locking mechanism, the locking mechanism having an opening to receive a portion of at least one of the first and second arms.

In accordance with another aspect of the present disclosure, a method of treating prolapse comprises: providing an implantable flat, flexible material having at least one arm extending from a side thereof; inserting the at least one arm through cervical tissue to form a cervical cerclage; and attaching a portion of the mesh to the sacrum.

In some embodiments the implantable flat, flexible material includes at least one eyelet.

In some embodiments the method further comprises inserting the at least one arm through the at least one eyelet.

In some embodiments the insertions are made with a needle disposed at distal end of the at least one arm.

In some embodiments the insertions are made proximate the cervical isthmus.

In some embodiments the at least one arm is inserted from a posterior to anterior portion of the cervical isthmus.

In some embodiments an implantable sacrocolpopexy medical device comprises an elongate base portion having a length extending longitudinally from a proximal end to a distal end; a sleeve disposed around at least a portion of the distal end of the base portion; a dilator disposed at a distal end of the sleeve; and a needle disposed at a distal end of the dilator.

In some embodiments the medical device further comprises a suture disposed between the dilator and the needle.

In some embodiments the medical device further comprises at least one suture loop attaching the dilator to the base portion.

In some embodiments the needle has a curved geometry.

In some embodiments a proximal end of the base portion includes an eyelet.

In some embodiments the medical device further comprises a locking mechanism, the locking mechanism having an opening to receive a portion of the elongate base portion.

In some embodiments a proximal end of the base portion has a larger surface area than a distal end of the base portion.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION

Figure 1:
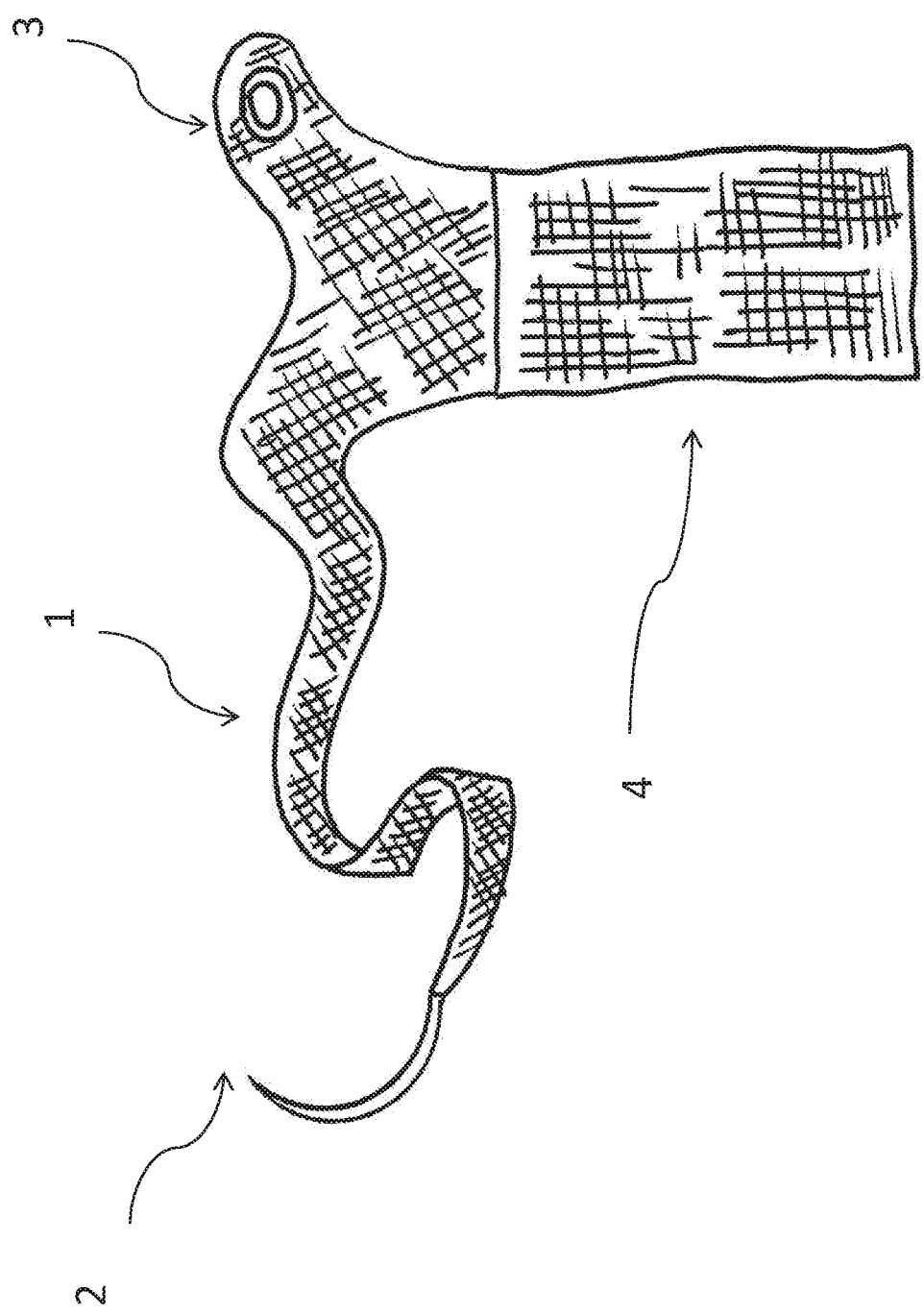
FIGS. 1-4 are schematic representations of exemplary embodiments of the medical device with a single mesh cerclage material arm in accordance with the disclosed subject matter.

The present disclosure describes a novel device and method for treating pelvic disorders, which in an exemplary embodiment, includes mesh design for apical support for the condition of uterovaginal prolapse. In accordance with another aspect of the present disclosure, a novel method is provided for performing the device in a completely transvaginal technique. Some exemplary embodiments are particularly suited to treat uterine prolapse while others are particularly suited for treatment of vaginal prolapse as they can include anterior or posterior extensions of the mesh.

In some embodiments, the device may comprise two components: a material that is used to create a cervical cerclage (or other type of attachment to the cervix), and an attached sacral extension. Additionally or alternatively, there may be a third component, which is an anterior and/or posterior extension when the surgeon wants additional coverage in those areas. The cerclage material may be suture, barbed suture, a molded material in a fishbone or other design that prevents slippage of the material back through the tissue, or may be a mesh material that has inherent self-adherence properties (for example, polypropylene or polyester mesh, similar to the TVT—tension-free vaginal tape—sling). At the end of the cerclage arm there may be a curved, straight, "ski" or other type of needle, which may be sharp or blunt-tipped to drive the cerclage material through the cervical tissue. The cerclage arm may have a plastic sleeve that assists with passage of the cerclage through the tissue (by reducing friction of the cerclage material against the cervical tissue), which can later be removed, leaving the cerclage material in place. The needle may be attached to some material (such as a polymer) that acts as a tapered dilator of the tissue, to transition from a needle to the cerclage (especially if the cerclage is a mesh) to assist with getting the material through the tissue.

In use the surgeon may perform the cerclage using a needle driver or other laparoscopic or open instrument, and may do this in as little as two bites (e.g. posterior to anterior and back from anterior to posterior), but this may also be done in multiple, smaller tissue purchases. In one exemplary technique, the surgeon would begin the cerclage posteriorly and would take successive tissue purchases to encircle the cervix, which may require passing the cerclage material medial to the uterine arteries on either side of the cervix (preferably at the level of the cervical isthmus). The cerclage would be completed posteriorly on the other side of the cervix and the surgeon may pass the cerclage material (still attached to the needle) through some mechanism on the mesh (e.g. an aperture, such as an eyelet) so that it completes the cerclage and can be cinched down without the need for tying a knot in the cerclage material. The cerclage material can then be trimmed so excess material is not sticking out from the eyelet on the mesh. Once this is complete, the sacral extension can be attached in traditional methods to the sacral promontory (anterior longitudinal ligament) or other apical supporting structure, such as the sacrospinous ligament. For example, the surgeon may use sutures or a tacking device to attach the sacral extension to the sacrum or sacrospinous ligament. It should be noted that the cerclage procedure may be performed either endoscopically (laparoscopic or robotic) or may be performed transvaginally.

If performed vaginally, the surgeon would make an incision anteriorly between the cervix and the proximal anterior vaginal wall, and would dissect the bladder off the anterior portion of the cervix, far enough to permit the cerclage material to lay flat on the cervix. An incision would also be made posteriorly and the rectum dissected off the posterior portion of the cervix, to allow the mesh to lay down flat against the cervix. An incision is also made in the peritoneum in the posterior cul-de-sac. The cerclage is then performed using a technique similar to the Shirodkar cerclage, keeping the cerclage material under the vaginal epithelium. After the cerclage is completed, the two ends of the cerclage material are exiting the cervical tissue posteriorly, and once the connection is made between the free end and the base of the mesh (part of the sacral extension), the sacral extension is placed through the incision in the cul-de-sac and into the pelvic cavity. Subsequent to this, the vaginal epithelial incisions are closed anteriorly and posteriorly and the remainder of the procedure can be performed abdominally (including laparoscopically or robotically). Alternatively, an instrument may be placed through a cannula placed transvaginally in the posterior cul-de-sac in order to introduce sutures and/or needles into the pelvic cavity or to fix the mesh to the sacrum directly using an instrument such as a tacking device.

Another vaginal technique that can be used is to place the cerclage in a manner similar to a Shirodkar procedure (as described previously), with the mid-portion of the mesh or fabric strip located on the anterior portion of the cervix and bringing the two ends of the mesh from the anterior to the posterior portion of the cervix with the use of needles (straight, curved, ski, or other) attached to the mesh, or with the use of an instrument, such as an Emmet-type needle with an eyelet, through which the ends of the mesh can be threated to facilitate transfer through the lateral cervical stroma. The two ends of the mesh arms, which exit posteriorly in the cervix, may be attached to one another to create a mesh extension that is twice the width of the mesh arm using one of several methods, such as interrupted sutures, a continuous suture, or hook-and-loop fasteners to unite the two edges, heat sealing or other method of attaching the two ends of the mesh. Attachment features integral to one or both arms may impede passage through the cervix, so one or both arms may be provided in removable sleeves, such as plastic sleeves, to facilitate passage. This wider mesh extension would then be placed into the posterior cul-de-sac and eventually attached to the sacrum (anterior longitudinal ligament), as is commonly done with a traditional sacrocolpopexy. In another embodiment, the mid-portion of the mesh strip is more narrow (approximately 1.5 cm wide) than the ends of the mesh strip (approximately 2 cm wide). The mid-portion of the mesh strip may be approximately 12 cm long so that the more narrow portion of the mesh can completely encircle the cervix with the cerclage technique, whereas the ends are wider, so the ends can be united to form a sacral attachment piece that is approximately 4 cm wide. In order to facilitate movement of the wider portion of the mesh through the cervix during the cerclage, the needle on each end of the mesh may have a molded piece between the needle and the mesh, which is tapered to permit smooth transfer of the mesh through the cervical tissue. The molded piece may attach to the end of the mesh strip in such a way as to fold the mesh strip in half so that for instance, rather than a 2 cm wide mesh, the mesh is folded over to become only 1 cm wide. The molded piece may be attached to a plastic sleeve that covers the wider portion of the mesh to facilitate transfer of the mesh through the cervix. This plastic would also function to help keep the mesh folded over.

In some embodiments the cerclage material may have two arms extending from either side of the sacral mesh extension. On the ends of either arm may be needles that may be driven from posterior to anterior cervix (preferably at the level of the cervical isthmus). Once the needles and attached cerclage material have been drawn to the anterior portion, the material (e.g. mesh, barbed suture) may be cut at the level of the cervix so that the material does not extend out from the cervical surface. A locking mechanism, such as a small plastic disc, may be placed over the arm material and placed flush up against the anterior cervix and act to prevent slippage of the arm back through the cervical tissue. Alternatively, the ends of the cerclage arms may have connectors attached. A needle device inserted through a laparoscopic or robotic cannula, or placed percutaneously through the abdomen (or directly, in the case of open surgery), or placed through a portion of the cervix when performed transvaginally may perforate the cervix from anterior to posterior, and then make a connection with the connector attached to the cerclage arm (e.g. ferule) and when withdrawn, pulls the mesh arm through the cervix, which may then be cut at the anterior surface of the cervix. Again, a plastic disc may be utilized to lock the mesh arm against the anterior cervical surface. These mesh arms may have a covering plastic sleeve, which would allow easier passage of the arm through the cervical tissue and would be removed once the material is in proper position, thus engaging the material within the tissue.

In some embodiments, for women after supracervical hysterectomy (either remote from surgery or when performed concomitantly), the device may have an anterior extension which is long enough to reach the anterior portion of the cervix, and potentially down further along the anterior vaginal wall, with one or more holes on either side. These holes may be reinforced (to prevent tearing) or may have eyelets, possibly with a mechanism that allows passage of the posterior mesh arm through without the ability of the mesh arm to back out from the eyelet.

The posterior extension may extend to the posterior surface of the cervix (or further to cover the posterior vaginal wall), and may then have two mesh arm extensions, suture, barbed suture, or a monofilament polymer in a fishbone configuration which may have needles or ferules attached at the distal ends. If mesh arms are employed, the mesh arms may have plastic sleeves covering the arms to facilitate passage of the mesh arms through the tissue. If a needle is employed at the ends of the arms, the needle would be driven from posterior to anterior cervix, and then would be placed through the holes/eyelets on the anterior mesh segment. The arms would be cut after passage though the anterior mesh segment.

A locking mechanism may be placed over the arms once they pass through the anterior mesh segment to prevent slippage back through the tissue. If a ferule is employed at the ends of the arms, a needle may be placed from anterior to posterior cervix, first passing through the anterior mesh segment hole/eyelet, then through the cervix, and then engage the ferule and withdraw the arm material through the cervix and up through the anterior mesh segment. A locking mechanism (which may have been preloaded on the needle) may then be cinched over the arm, locking it in place and preventing backing of the arm through the cervix. Once the cervix has been secured bilaterally, the sacral mesh segment would be fixed to the sacrum in standard fashion, as previously described.

In some embodiments, a similar design as described above for supracervical hysterectomy could have an anterior extension with eyelets in the proximal anterior extension, but could have a longer anterior segment, which could cover some part of the anterior vaginal wall and be sutured to the anterior vaginal wall. Similarly, there may be a posterior mesh extension that could cover some part of the posterior vaginal wall and be sutured thereto.

In some embodiments, whether or not a supracervical hysterectomy has been performed, a separate anterior mesh segment with eyelets may be included in the system. The mesh arms that are brought from posterior to anterior (either as a cerclage or directly from posterior to anterior as described earlier) can be passed through the eyelets of the anterior mesh segment (with or without an additional locking mechanism) and then the rest of the anterior mesh segment may be sutured to the anterior vagina and lower aspect of the cervix using traditional laparoscopic suturing.

The cerclage may be performed transvaginally in the following manner. A tenaculum or other grasping instrument may be placed on the cervix and an incision is made on the anterior cervical vaginal junction. The bladder is advanced off the cervix and lower uterine segment, as is done during the first stage of a vaginal hysterectomy. A posterior incision may also be made and at some point, and entry into the posterior cul-de-sac is made. Alternatively, a complete circumferential incision may be made around the cervix to advance the vaginal epithelium off the cervix. The needle attached to the narrow cerclage mesh is used to create a cerclage into the cervix. For example, a purchase may be made posteriorly, and then laterally, avoiding the uterine arteries by going into the stroma of the cervix. One or more tissue bites would then be taken anteriorly and then on the opposite lateral side of the cervix. Finally, the needle would be passed through the hole or grommet on the body of the mesh. Alternatively, there may be some device on the base of the mesh that locks the cerclage in place. Alternatively, the mesh strip may be sutured to the base of the mesh with permanent or delayed absorbable sutures. At this point, the needle and excess mesh would be removed from the device leaving the sacral tail extension.

In some embodiments with two cerclage arms, each with needles on the ends, purchases of the cervix could be made laterally from posterior to anterior and then into the anterior cervix; these could occur at slightly different levels on the anterior cervix so that the mesh arms do not intersect with one another and may overlap. The arms would stay in place by friction between the mesh arms and the cervical tissue. Alternatively, the mesh arms may overlap on the anterior cervix and be sutured together in that location, potentially with a permanent or delayed absorbable suture.

In some embodiments, the system comprises straight piece of sling-like mesh with one end attached to a curved needle, possibly with a protective plastic sleeve, leading to a plastic dilator, which is attached to a curved needle, such as CT2 or CT1. On the other end of the mesh device is a reinforced grommet, possibly with a narrow slit to lock the mesh in place. Other locking mechanisms may also be used. When the needle and mesh are placed through the cervix in a cerclage-fashion, the needle is placed back through the center of the grommet, the cerclage is tightened and the needle and plastic sleeve is removed from the rest of the mesh. The tail of the mesh is placed into the pelvic cavity and, if the case is to be completed laparoscopically or robotically, the vaginal incision is closed. If the case is to be completed vaginally, the procedure proceeds either endoscopically or purely vaginally.

For embodiments employing the endoscopic technique, a trocar cannula would then be placed up through the anterior or posterior incision into the cul-de-sac. This cannula may have a balloon or foam tip, or other mechanism, that maintains pneumoperitoneum. The pelvic cavity would then be insufflated, enabling the surgeon to view the right pelvic sidewall and sacral promontory. At this point, the surgeon would have several alternative options. First, a small incision could be made on the right pelvic sidewall and a blunt instrument could be used to dilate a tunnel up to the sacral promontory while observing this endoscopically through the transvaginal cannula. Both the blunt instrument and the laparoscope may be placed through a single port in the cul-de-sac. The sacral tail could then be placed with a grasper into the tunnel and up to the sacrum and the some fixation device, such as a spiral tacker may be used to fix the sacral tail to the sacrum. Alternatively, after determining the proper tension on the mesh, the spiral tacker could be used to pick up the proper length of the sacral tail (by partially deploying the tack) and bring the mesh arm up to the sacrum, where it would be attached.

Alternatively, the tip of the cannula could be placed into this incision and insufflation of the retroperitoneum could be performed. This would allow the tacking to be performed under direct visualization, rather than indirectly through the peritoneum.

Alternatively, under direct visualization, an incision could be made along the right pelvic sidewall up to the sacral promontory. After attaching the mesh to the sacrum using either a spiral tacking device or suture, or other device, the peritoneum could be closed over the mesh in one of several ways, including surgical staples or clips that are placed along with the laparoscope through the transvaginal port, as in single-port surgery.

Alternatively, once the vaginal cerclage is placed, the surgeon could place the sacral tail into the abdominal cavity, and then proceed laparoscopically or robotically with fixation of the sacral tail to the sacral promontory. This may involve opening up the right pelvic sidewall and peritoneum over the sacral promontory. If the surgeon were to use a vaginal trocar as described earlier, a fixation device such as a spiral tacker could be placed transvaginally with laparoscopic guidance, which may provide a more anatomic approach to correct sacral fixation. If some instances, the sutures may be tied intracorporeally or extracorporeally either through the transvaginal cannula or through one of the laparoscopic cannulas. The peritoneum may then be closed over the mesh by inserting the suture and needle through the transvaginal cannula.

Thus, in accordance with an aspect of the present disclosure, a system is provided for performing sacrohysteropexy or sacrocervicopexy, which can be performed open, laparoscopically or robotically. In some embodiments, the system has at least two components: a material and needle for performing a cervical cerclage (or passage through the cervical tissue); and a sacral mesh extension. The device can be employed to treat uterine prolapse, by supporting the apex of the vagina (i.e. cervix) by encircling the cervix with a cerclage material or by passing the material through the cervix, and then attaching the cerclage to the sacral area with the use of an intervening mesh extension. This procedure can be performed with or without supracervical hysterectomy, but does require that the cervix, or at least some portion of the cervix, be present, in order to perform the cerclage. Performing the cerclage at the isthmus of the cervix (the cervico-uterine junction) serves to reduce, or eliminate, the risk of erosion/exposure of the cerclage into the vagina. The surgery may involve dissection of the bladder off the lower cervical segment, although in some women, no dissection may be necessary if the bladder is found not to be adherent to the upper cervix. After introduction of the device into the pelvic cavity (and dissection of surgical spaces as needed), the surgeon may perform a cerclage with the cerclage material.

The cerclage material may be comprised of mesh, suture, barbed suture, a material with a fishbone configuration, or other material that may prevent the cerclage from backing out through the cervical tissue. An eyelet in the body of the mesh may assist with stabilization of the cerclage. The cerclage material can be attached to the sacral mesh extension, which could then be attached to the sacrum (e.g. anterior longitudinal ligament of the sacrum) in one of several methods, such as suturing or tacking.

In another embodiment, there may be two arms extending from either side of the sacral mesh extension. These two arms may be constructed of mesh, suture, barbed suture, a material with a fishbone configuration, or other material that may prevent the material from backing out through the cervical tissue.

The two arms may have attached needles, each of which may be drawn through the cervical tissue, or alternatively, the two arms may have connectors (ferules) attached. The surgeon would then have to pass a needle (such as a straight needle) either through a laparoscopic or robotic cannula, or percutaneously through the abdomen, or directly through an abdominal incision, which would pass through the cervix, on one of both sides, and make a connection with the ferule connectors, and then withdrawal of the needle would pull the arms through the cervical tissue. The arms could then be cut at the level of the cervix.

Exemplary Illustrated Embodiments

Reference will now be made in detail to exemplary embodiments of the disclosed subject matter, examples of which are illustrated in the accompanying drawings. The method and corresponding steps of the disclosed subject matter will be described in conjunction with the detailed description of the system.

In accordance with an aspect of the present disclosure, the device generally includes a base portion having a length extending from proximal end and a distal end, and a width extending from a first side to a laterally opposed second side. The base portion can be formed with one or more bulbous projections at the distal end, to form a Y-shape base portion. An arm extends from a side of the base portion, and proximate the distal end of the base portion, a distance greater than the width of the base portion. The length of the arm can vary to accommodate different patient anatomies, but is sized and shaped so that it can be configured to extend around the cervical isthmus in an undulating fashion to form a cerclage. In some embodiments, the arm has a length that is sufficient to be configured into an annular band surrounding the entire perimeter of the cervical isthmus. In some embodiments the arm has a length that is sufficient to extend along only a single side of the cervical isthmus. In some embodiments the base portion and arm are formed as separate components, which can be made from homogenous or distinct materials. For instance, the base portion can be formed of woven fixed-length fibers, and the arm can be formed of a material with greater elasticity than the base portion. In such embodiments the arm can be coupled to an edge of the base portion. In other embodiments the base portion and arm are integrally formed as a unitary member. In some embodiments the base portion can be provided with sufficient length so that the proximal end can be attached to the sacrum or other apical structure. In some embodiments the base portion can include a discrete sacral mesh extension.

As mentioned above, the materials used to make the various portions may have a variety of elasticities. For example, the portion that forms the cerclage may be relatively inelastic in the longitudinal axis of the cerclage. The portion that extends to the sacrum similarly may be inelastic in the longitudinal axis toward the sacrum. A material such as mesh is made inelastic in a particular direction by orienting the fibers orthogonal to the direction of desired inelasticity, i.e., fibers arranged in a rectangular or square pattern with the sides oriented parallel and perpendicular to the direction of desired inelasticity. This type of material can be made elastic by orienting the fibers at an angle transverse to the direction of desired elasticity, such as a 45-degree angle, such as in a diamond pattern.

As shown in FIG. 1, the base portion (4), which is configured for attachment to, e.g., a sacrum, includes a mesh arm (1), which serves as the cerclage material for attachment to the cervical isthmus. The arm (1) can include a needle (2) on the distal end which assists in the piercing of tissue when performing the cerclage around the cervical isthmus, or portion thereof. Additionally, the base portion can include an eyelet (3) located near a side opposite of the arm (1), and at the distal end of the base portion. The arm (and needle if present) can be advanced through the tissue to form a cerclage and received through the eyelet (3). The mesh arm (1) can be formed with a tapered shape, as shown, so that frictional forces are increased as the mesh arm is inserted through the eyelet (3). The eyelets disclosed herein can be reinforced to increase the strength and elasticity by providing additional (localized) layers of material around the opening, or by coupling a separate ring of bio-compatible material around the opening. The exemplary embodiment shown can be integrally formed as a unitary member in which the base portion (4) and arm (1) are a single piece. Alternatively, the base portion (4) and arm are formed as separate components. Additionally, the base portion (4) can itself be formed as two discrete components, one forming a Y-shaped member and the other forming a sacral extension.

Figure 2:
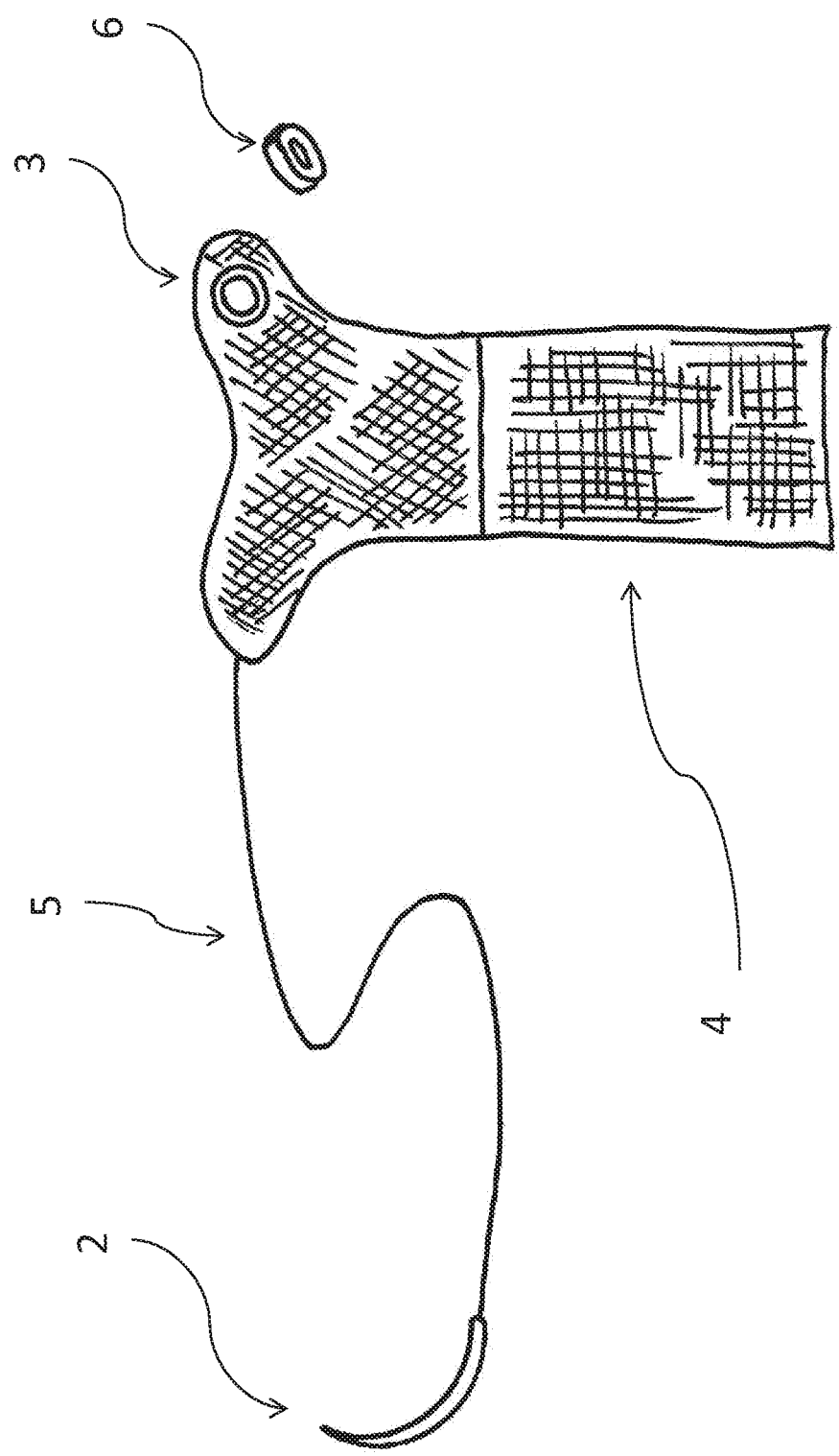

FIG. 2 depicts another exemplary embodiment in which the arm is formed as a suture cerclage (5). The suture cerclage arm can include a needle (2) on the distal end, and an eyelet (3) on the body of the base portion. Additionally, a locking mechanism (6) can be coupled to the end of the suture cerclage arm (5) after it is passed through the eyelet (3). The locking mechanism may be made of a material, such as titanium, that can be crimped around the suture with the use of a grasping or clamping device. In some embodiments a permanent lock can be included to prevent slippage of the suture back through the eyelet. The locking mechanism can be sized with an aperture to receive a portion of the suture cerclage arm (5), and/or needle (2) if present, to ensure that the suture does not pull back through the cervical tissue.

Figure 3:
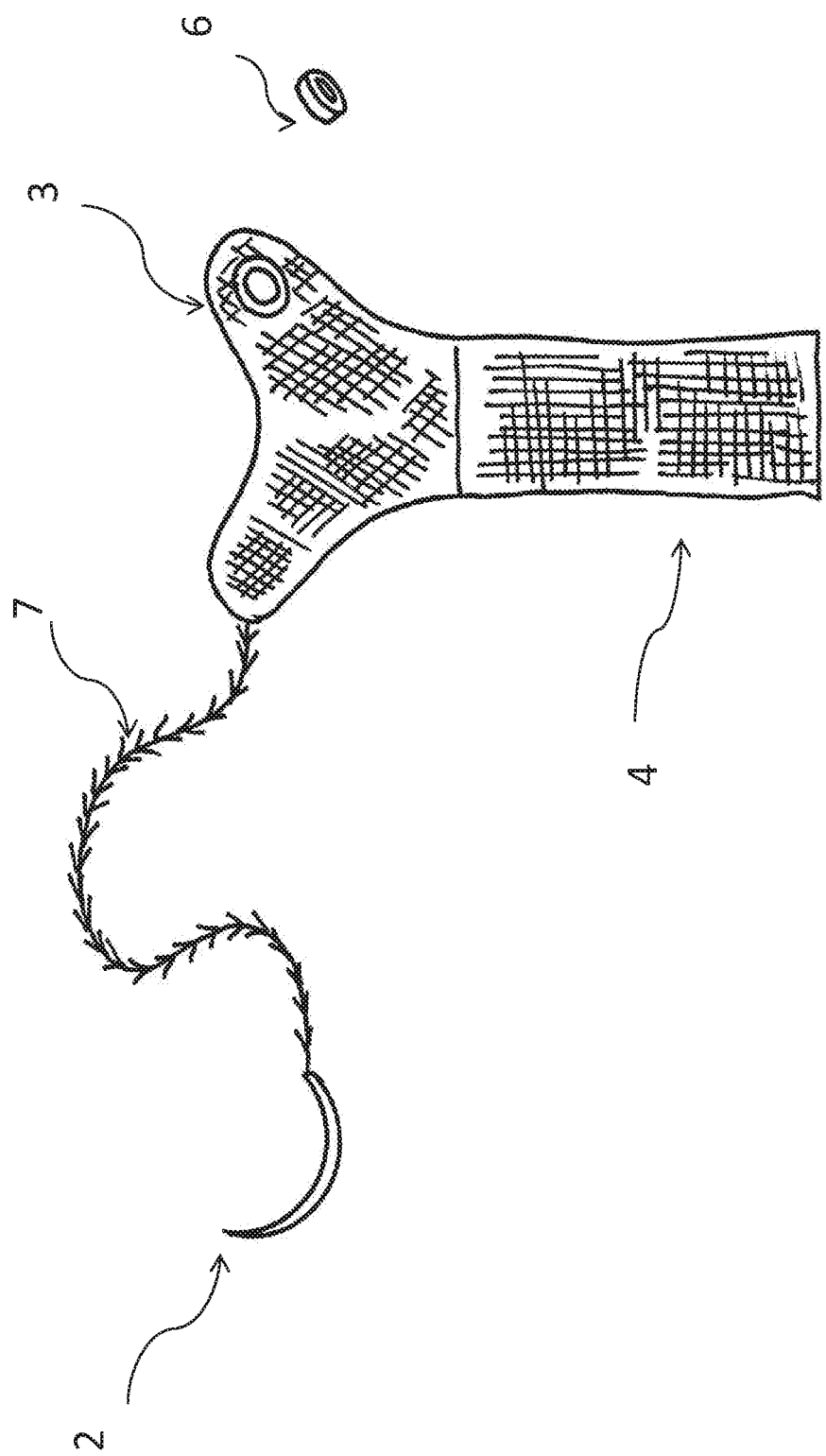

FIG. 3 depicts another exemplary embodiment, wherein the arm includes retention features, e.g., barbs projecting outward from the arm. The barbs can project in a uniform, or non-uniform (e.g. at a variety of different angles with respect to the arm), and at varying lengths as so desired. As such, the arm is configured as a barbed suture cerclage (7). Additionally, and as previously described, a needle (2) can be included on the end of the barbed suture cerclage (7), and an eyelet (3) can be included on the body of the base portion (4). Also, and as previously described, a locking mechanism (6) can be added to the end of the suture after passing through the eyelet (3), to ensure that the suture does not pull back through the cervical tissue.

Figure 4:
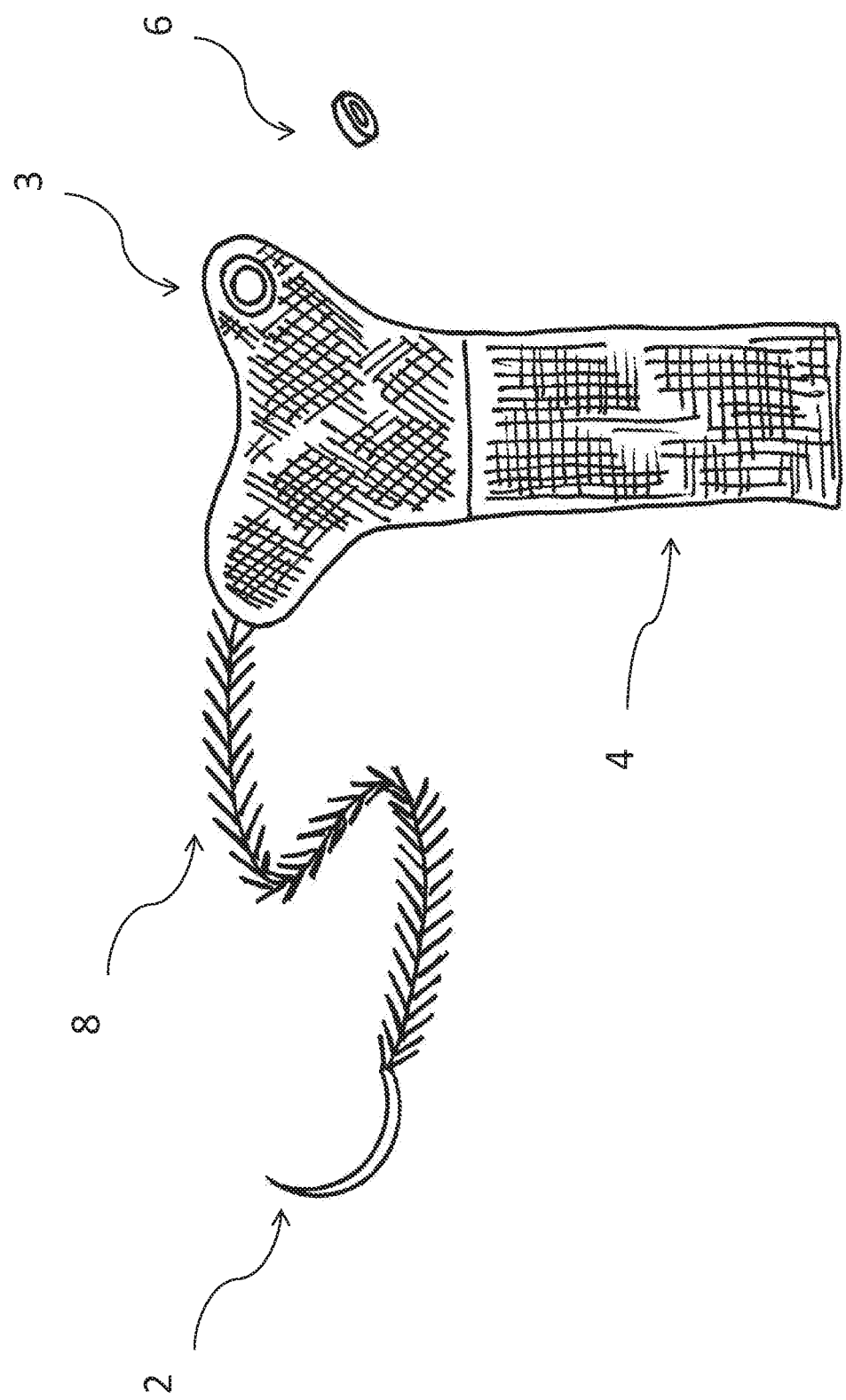

FIG. 4 depicts another exemplary embodiment, wherein the arm includes retention features, e.g. a fishbone-shaped projection. The fishbone projections can each be oriented in the same direction with respect to the arm, lie within the same plane, and have a uniform length. As such, the arm is configured as a monofilament cerclage device (8). Additionally, and as previously described, a needle (2) can be included on the end of the monofilament cerclage (8), and an eyelet (3) can be included on the body of the base portion (4). Also, and as previously described, a locking mechanism (6) can be added to the end of the suture after passing through the eyelet, to ensure that the cerclage material does not pull back through the cervical tissue.

Figure 5:
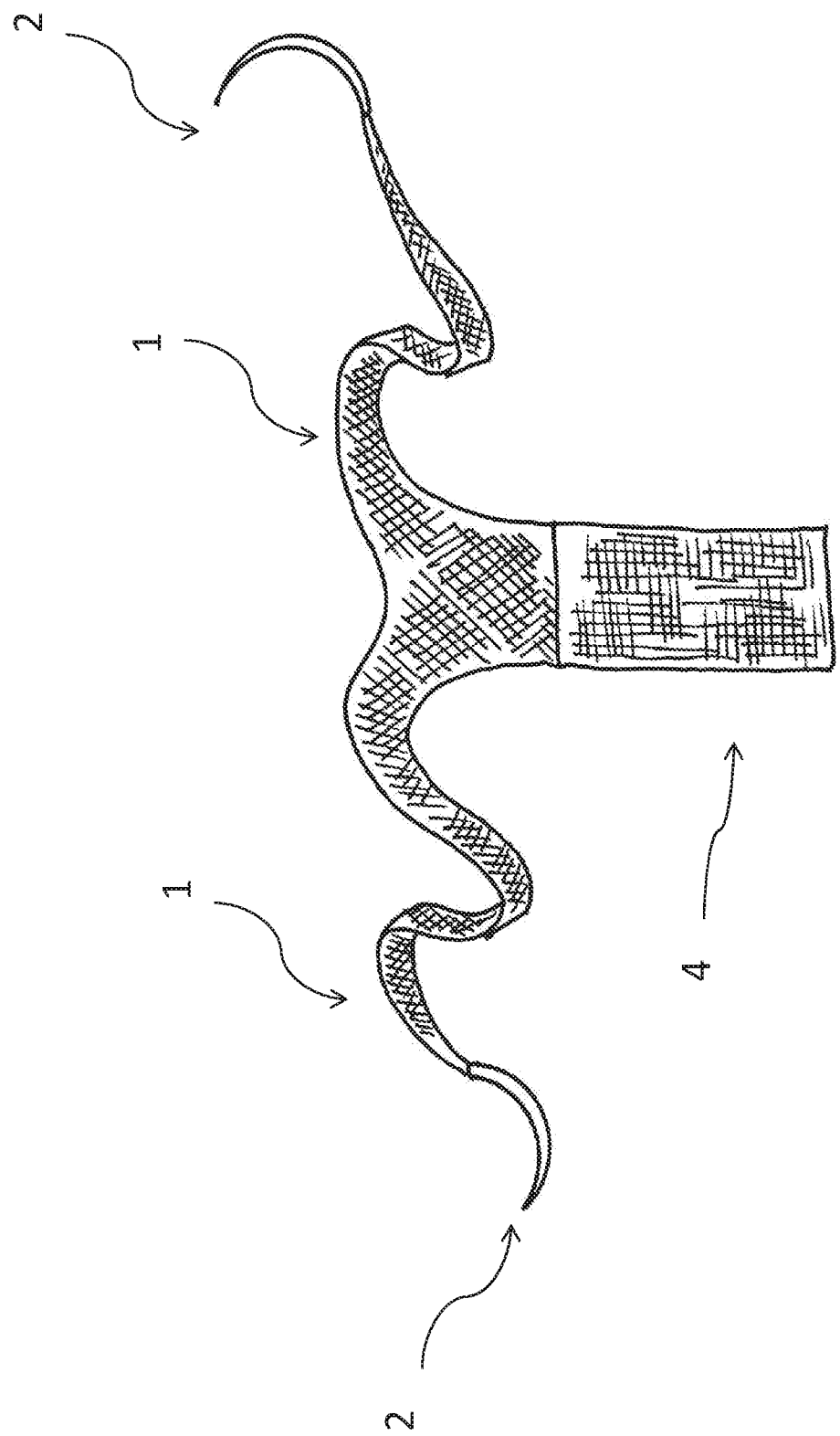
FIGS. 5 and 7 are schematic representations of exemplary embodiments of the medical device with a plurality of mesh cerclage material arms in accordance with the disclosed subject matter.

FIG. 5 depicts another exemplary embodiment, wherein two mesh cerclage arms (1) are provided, each extending outward from a side of the base portion (4). Additionally, and as previously described, a needle (2) can be attached to the ends of the arms (1). During operation, the arms (1) can be driven from posterior to anterior cervix on either side of the cervix, and then the mesh may be cut at the anterior surface of the cervix.

Figure 6:
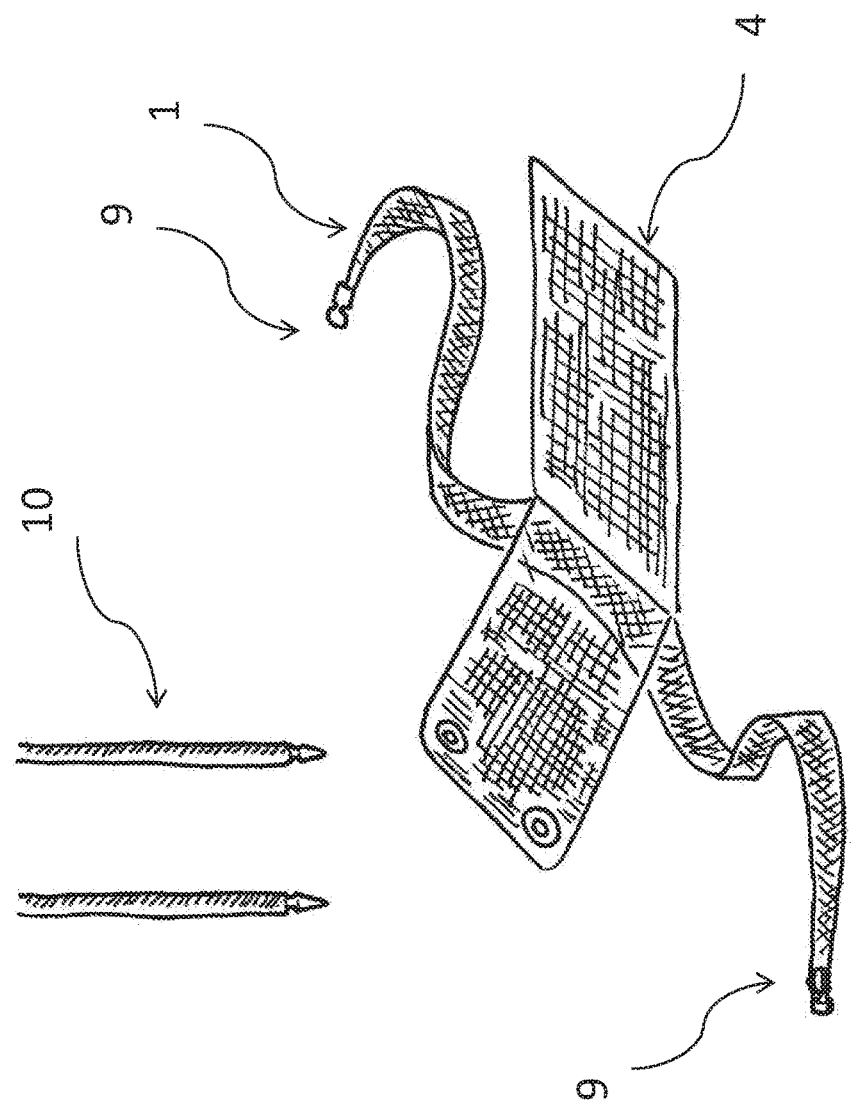
FIGS. 6 and 8 are schematic representations of exemplary embodiments of the medical device with a plurality of mesh cerclage material arms and needles in accordance with the disclosed subject matter.

FIG. 6 depicts another exemplary embodiment, wherein the two mesh arms (1), include a plastic or metallic connector (e.g. plastic or metallic ferule) (9) attached at the distal ends. The needle device may have one or more concentric rings that engage within the plastic or metallic ferule so that an irreversible attachment is made between the needle and the ferule, enabling the mesh arms to be drawn up along with the needle. Exemplary arrangements of needles and ferrules are shown in FIGS. 4, 10a-c, and 13 of U.S. Pat. No. 6,612,977, the cited portions of which are hereby incorporated herein by reference. During operation, a needle device (10) is driven through an eyelet on the anterior mesh extension, and then from anterior cervix to posterior cervix on either side of the cervix, which then makes a connection with the connector (9) and draws the mesh arm up through the cervical tissue, through the eyelet (3), and then the mesh may be cut at the anterior surface of the cervix. For example, in some embodiments the sacral mesh extension may be approximately 12 cm in length, and the anterior mesh extension, can be approximately 4 cm in length.

Figure 7:
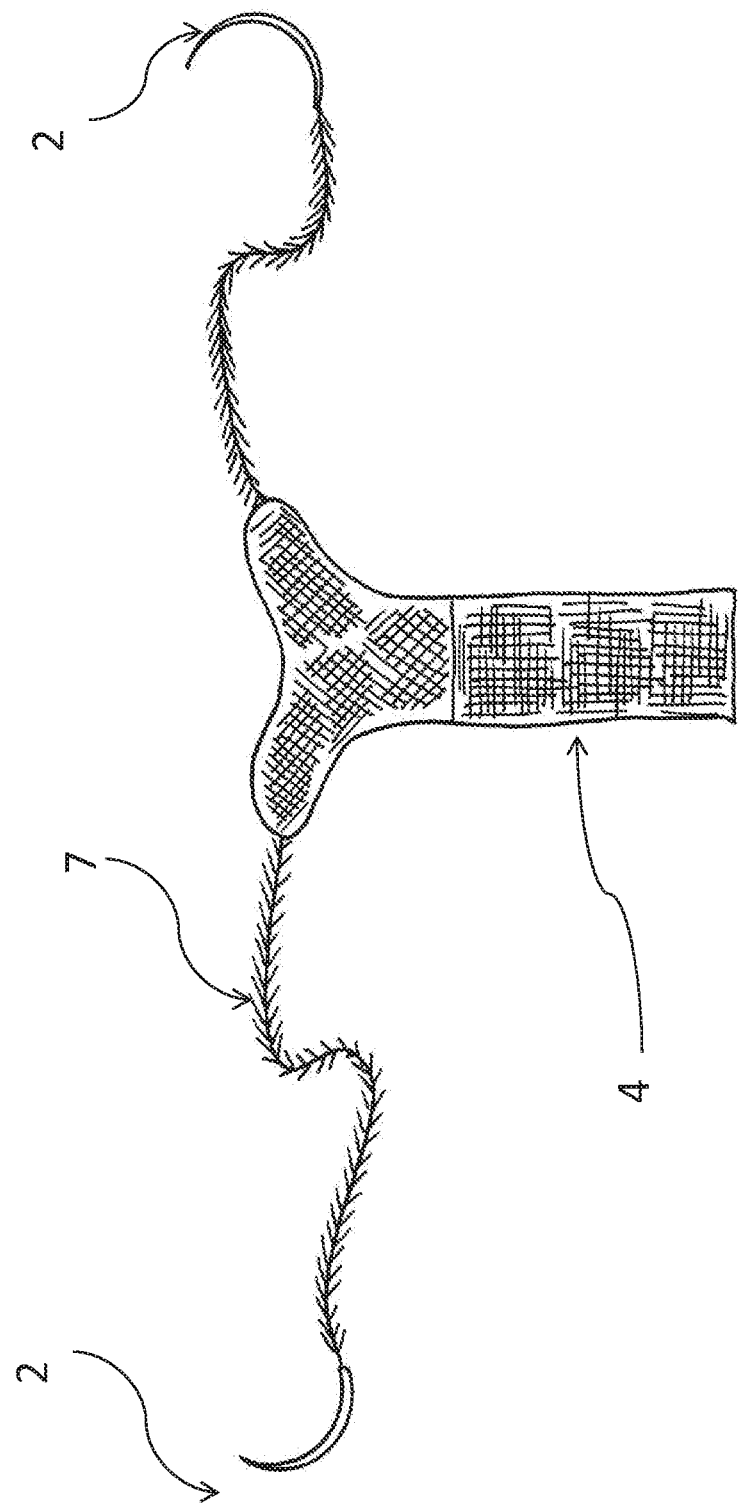

FIG. 7 depicts another exemplary embodiment, wherein two arms (7) are provided with retention features (e.g. barbs or fishbone elements) so that the arms are configured as barbed or fishbone monofilament arms (7). Additionally, and as previously described, a needle (2) can be attached to the distal ends of the arms (7) which can be driven from posterior to anterior cervix on either side of the cervix, and then the arms may be cut at the anterior surface of the cervix.

Figure 8:
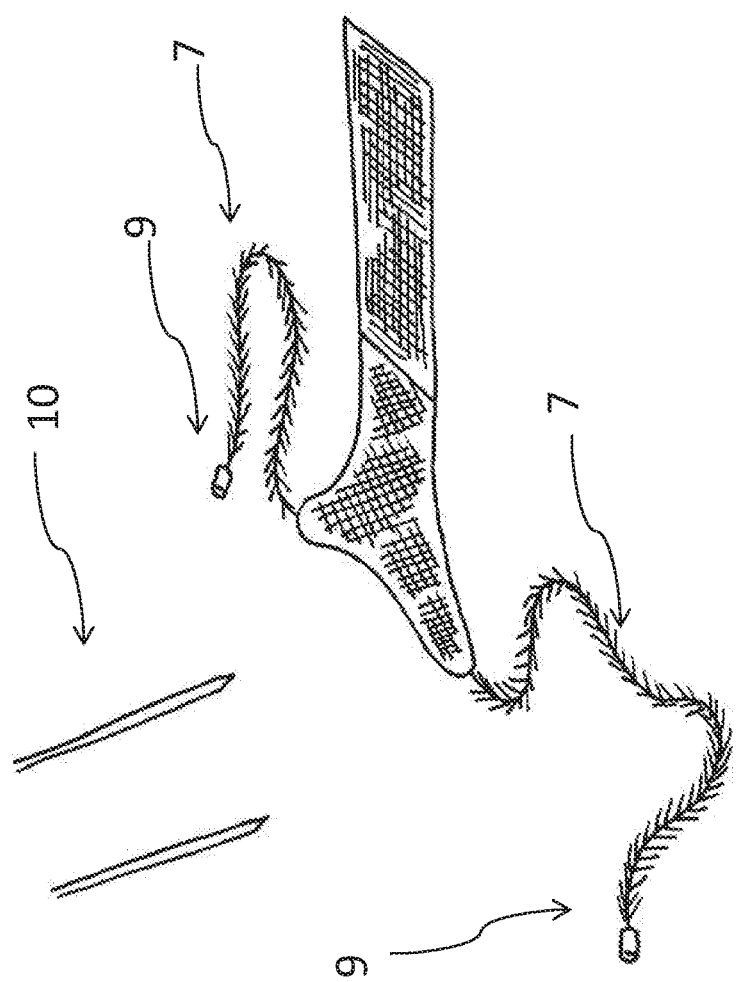

FIG. 8 depicts another exemplary embodiment, wherein two arms (7) are provided with retention features (e.g. barbs or fishbone elements) so that the arms are configured as barbed or fishbone monofilament arms (7). Additionally, and as previously described, the arms (7) can each be attached to a connector (9). A needle device (10) is driven from anterior cervix to posterior cervix on either side of the cervix, which then makes a connection with the connector (9) and draws the arm (7) up through the cervical tissue, and then the arms may be cut at the anterior surface of the cervix.

Figure 9:
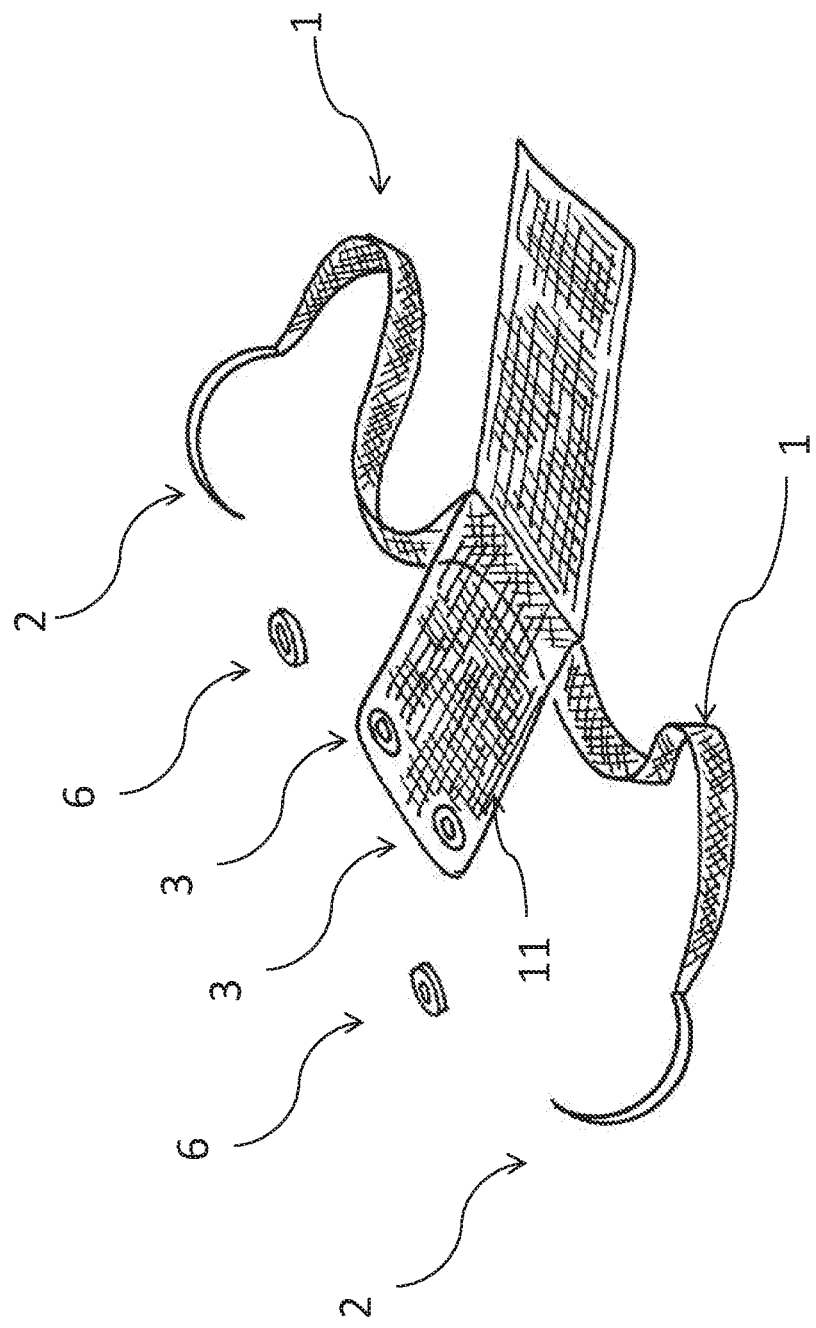
FIGS. 9, 10 and 12 are schematic representations of exemplary embodiments of the medical device with a plurality of mesh cerclage material arms, and anterior mesh extension, in accordance with the disclosed subject matter.

FIG. 9 depicts another exemplary embodiment, wherein the base portion, which serves as a sacral portion (4) to be attached to the sacrum, includes an anterior portion (or extension) (11). The anterior mesh extension (11) can be formed as a separate element from the sacral portion (4), and made of different material. Alternatively, the sacral portion (4) and anterior mesh extension (11) can be integrally formed as a unitary member. The sacral portion (4) can be formed with a length and width that is substantially equivalent to a length and width of the anterior mesh extension (11). If formed separately, the distal edge of the sacral portion (4) can be coupled to the proximal edge of the anterior mesh extension (11). As shown, two arms (1) are provided with distal needles (2) and extend from the sides of the anterior portion (11). Alternatively, the arms (1) can extend from the sides of the sacral portion (4). Additionally or alternatively, the arms (1) can be formed as a separate portion from the sacral mesh portion (4) and anterior portion (11) such that the arms (1) serve a posterior portion that extends a shorter length than the sacral mesh portion (4) and anterior portion (11). As previously described, the anterior mesh extension (11) can include two or more eyelets (3), through which the mesh arms (1) are placed and a locking mechanism (6) may be used to help affix the arms to the anterior mesh segment.

Figure 10:
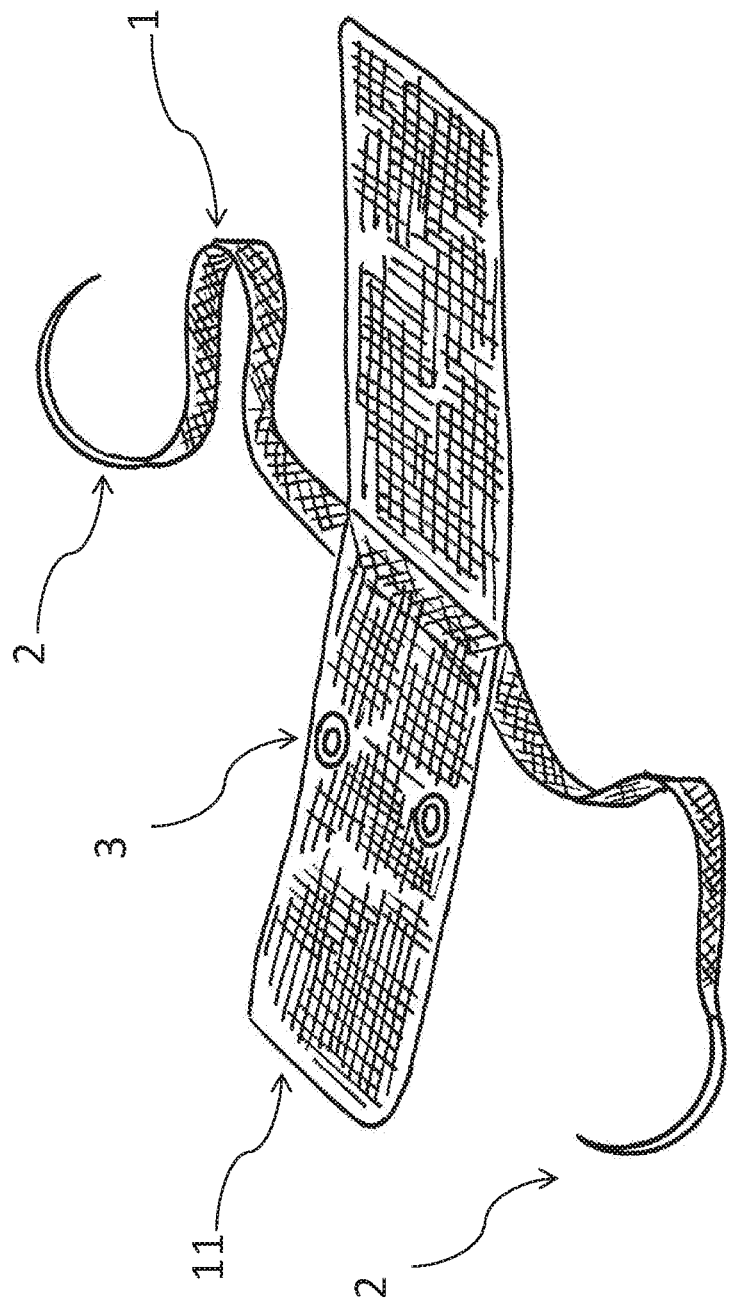

FIG. 10 depicts another exemplary embodiment, similar to the embodiment described in FIG. 9, wherein an anterior portion (or extension) (11) is employed which is particularly suited for use after supracervical hysterectomy, in which the surgeon elects to extend the anterior mesh extension (11). In this embodiment, the proximal anterior mesh extension (11) may have two mesh arms (1) with needles (2) extending from the sides thereof. Alternatively, the arms (1) can extend from the sides of the sacral portion (4). The mesh arms (1) may be placed in a cerclage fashion from anterior to posterior cervix, or may be brought directly through the cervix from posterior to anterior cervix, and then the mesh arms (1) may pass through eyelets (3) on the anterior mesh extension (11). The anterior mesh extension (11) may extend to cover more of the anterior vaginal wall. It is noted that the location of the eyelets (3) can vary as desired and depending on the particular cerclage technique employed by the physician. As shown in FIG. 9, the eyelets (3) can be located at a distal end of the anterior mesh extension (11). Conversely, and as shown in FIG. 10, the eyelets (3) can be located closer to the proximal edge of the anterior mesh extension (11).

Figure 11:
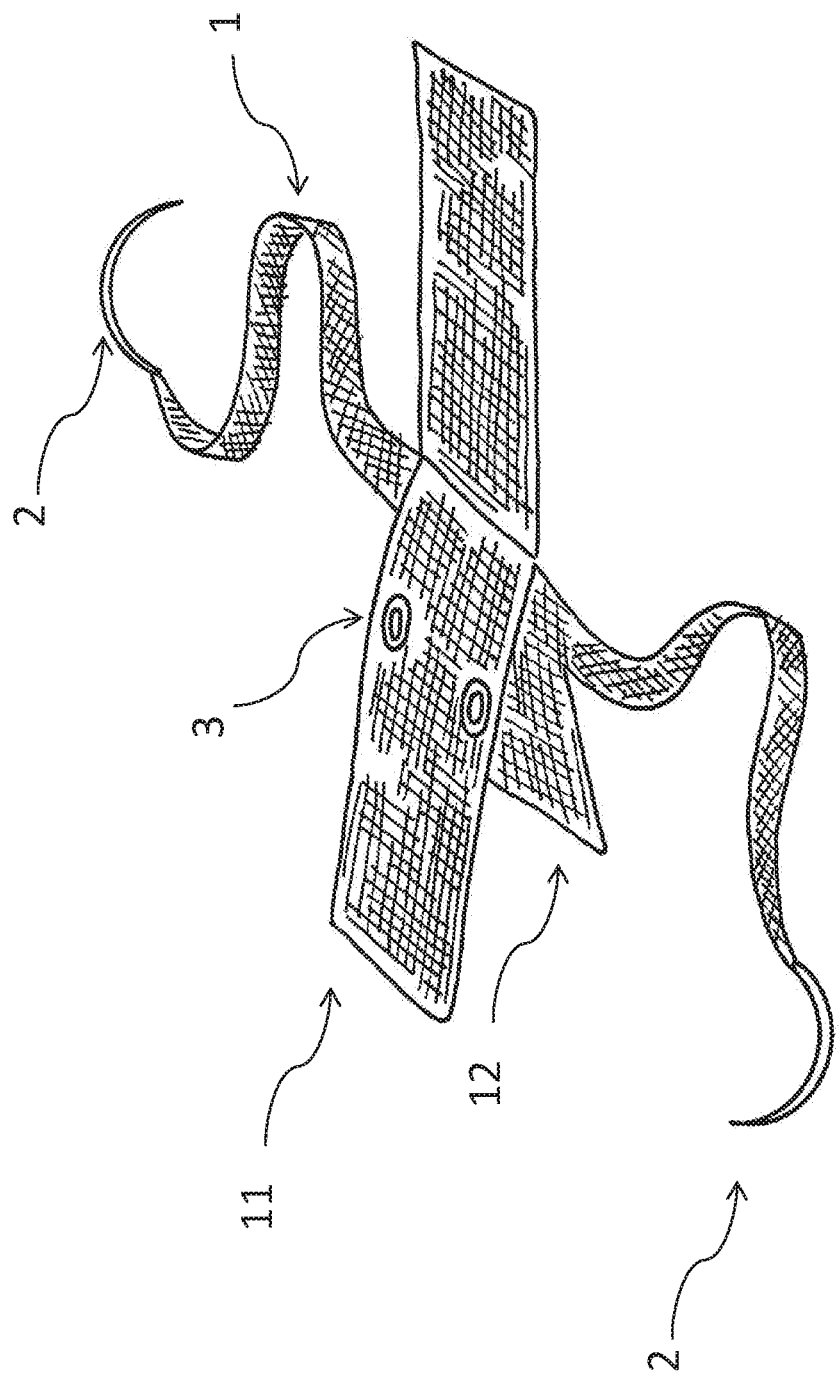
FIGS. 11 and 13 are schematic representations of exemplary embodiments of the medical device with a plurality of mesh cerclage material arms, anterior mesh and posterior mesh extensions, in accordance with the disclosed subject matter.

FIG. 11 depicts another exemplary embodiment, similar to the embodiment described in FIG. 10 above, further including a posterior portion (or extension) (12) that may extend over more of the posterior vaginal wall. In some embodiments, the sacral portion (4), anterior portion (11) and posterior portion (12) are configured with substantially equivalent length and widths. As shown, the arms (1) extend from the sides of the posterior portion (12). Alternatively, the arms (1) can extend from the sides of the sacral portion (4), or sides of the anterior portion (11).

Figure 12:
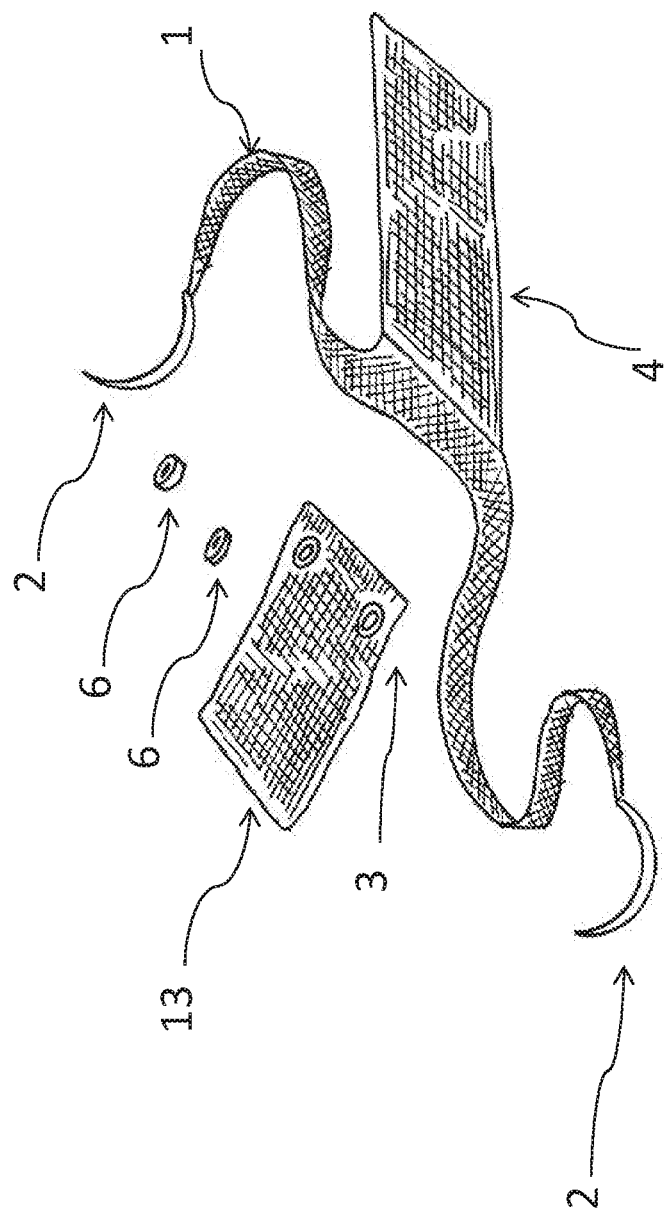

FIG. 12 depicts another exemplary embodiment, which may be used with or without supracervical hysterectomy. Similar to the embodiments described in connection with FIGS. 9-11, a sacral portion (4) has two mesh arms (1) with needles (2), which may be placed from posterior to anterior cervix either in a cerclage fashion or directly from posterior to anterior cervix. Additionally, an anterior portion (or extension) (13) is formed as a separate segment with eyelets (3) and is placed anteriorly. A proximal edge of the anterior portion (13) can be coupled to the distal edge of the sacral portion (4), or directly to the arms (1), as shown. The mesh arms (1) are brought up through the proximal eyelets (3) on the anterior portion (13) and are either self-locking, or additional locking devices (6) may be placed over the mesh arms (1). In operation, the anterior portion (13) may be sutured into position on the anterior vaginal wall after the bladder is dissected off the anterior vagina.

Figure 13:
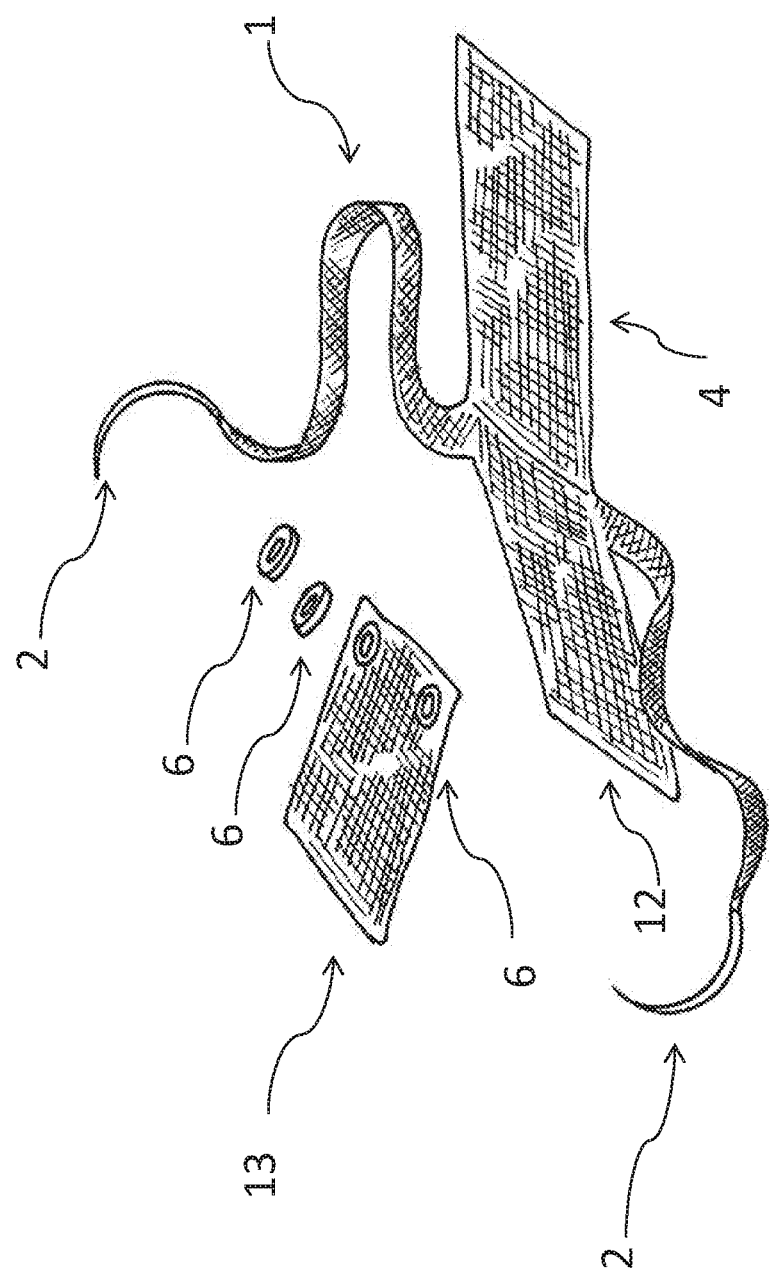

FIG. 13 depicts another exemplary embodiment which may also be used with or without supracervical hysterectomy. Similar to the embodiment described in connection with FIG. 12, a posterior portion (12) has two mesh arms (1) extending from its sides with needles (2), which may be placed from posterior to anterior cervix either in a cerclage fashion or directly from posterior to anterior cervix. Alternatively, the arms (1) can extend from the sides of the sacral portion (4), or sides of the anterior portion (11). A separate base portion (13) with eyelets (3) is placed anteriorly. The arms (1) of the posterior portion (12) are brought up through the proximal eyelets (3) on the anterior portion (13) and are either self-locking, or additional locking devices (6) may be placed over the mesh arms (1). The anterior portion (13) may be sutured into position on the anterior vaginal wall after the bladder is dissected off the anterior vagina. The posterior portion (12) may have an attached posterior portion (12) that extends down the posterior vaginal wall.

Figure 14:
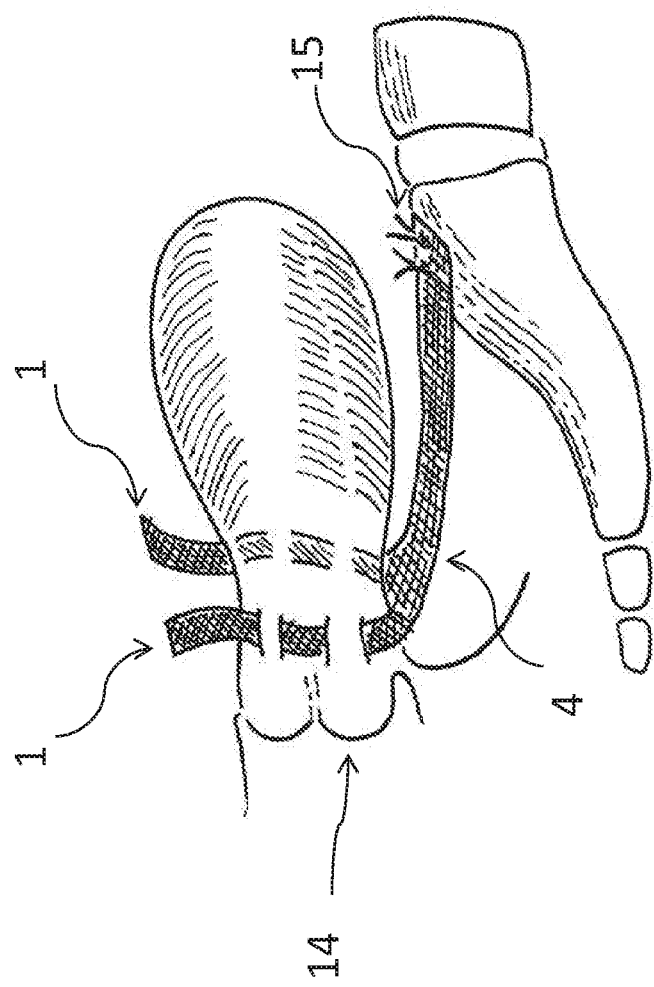
FIGS. 14 and 15 are schematic representations of exemplary embodiments of the method of operating the medical device, in accordance with the disclosed subject matter.

FIG. 14 depicts the operation of the device as described in connection with FIG. 5, with the cerclage arms (1) having been placed from the posterior to the anterior portion of the cervical isthmus (14) and the sacral mesh segment (4) attached to the sacral promontory (15).

Figure 15:
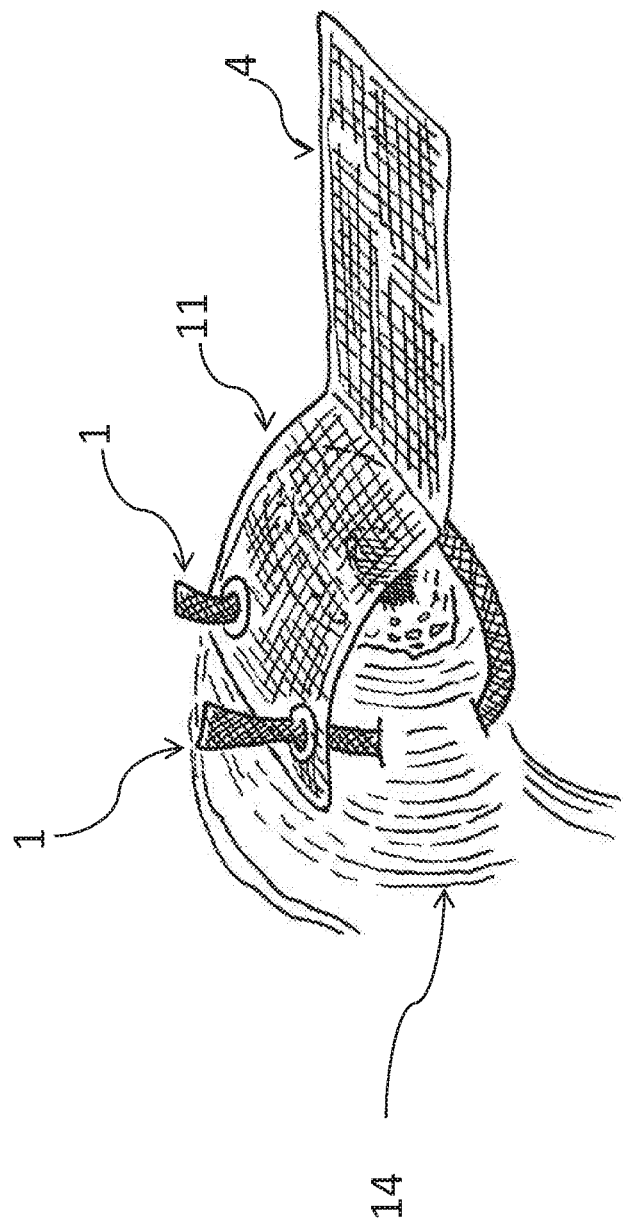

FIG. 15 depicts the operation of the device as described in connection with FIG. 9, with the cerclage arms (1) having been placed from the posterior to the anterior portion of the cervical isthmus (14) and then up through the eyelets (3) on the anterior mesh extension (11). The sacral portion (4) would extend up to the sacral promontory.

Figure 16:
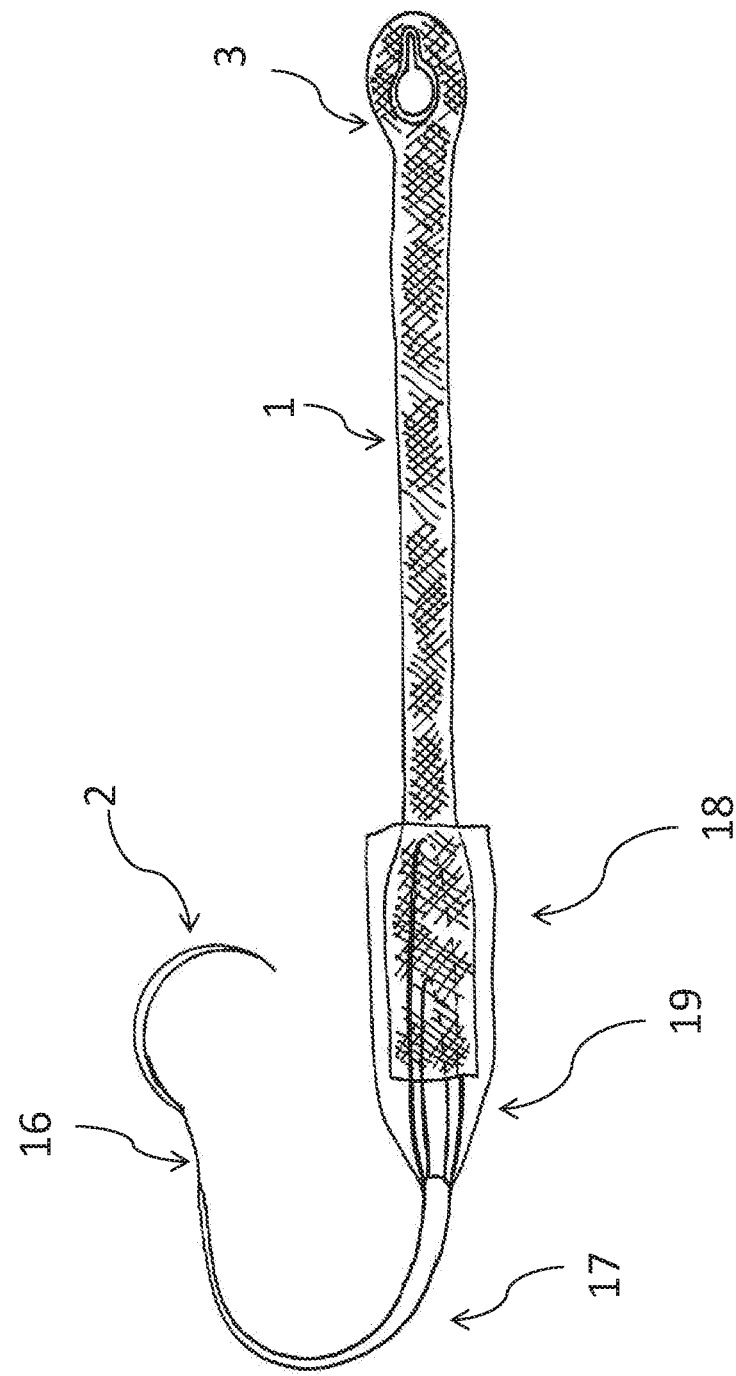
FIG. 16 is a schematic representation of exemplary embodiment of the medical device with a base portion, sleeve, dilator and needle, in accordance with the disclosed subject matter.

FIG. 16 depicts another exemplary embodiment in which an elongated mesh (1) is provided with a curved needle (2) at a distal end. The radius of curvature of the needle can be selected dependent upon the particular patient anatomy. The needle (2) can be attached to a monofilament or multifilament suture (16), which may either be absorbable or non-absorbable, which is attached to a plastic dilator (17), which is attached to a plastic sleeve (18), with one or more suture loops (19) holding the mesh to the plastic dilator. The suture loops, which may be made from a monofilament suture, pass through the interstices of the mesh to prevent the mesh from slipping out of the plastic sheath. On the other (proximal) end of the mesh is a grommet or eyelet (3). The eyelet, which can include reinforced material as described above, receives the needle after the cerclage has been performed. The eyelet (3) can be formed with a non-uniform geometry with a distal portion of the eyelet having a larger and generally circular opening, while a more distal portion of the eyelet is formed with a more narrow, and linear slot. Additionally, the eyelet (3) may have a mechanism that assists in locking the mesh in place to prevent it from slipping back through the eyelet. For instance, the proximal end of the mesh strip (1), which is to be attached to the sacrum or other apical structure, such as the sacrospinous ligament, may be wider than the portion of the strip of mesh (1) that is used as a cerclage. Such a configuration is advantageous in that it provides a larger surface area for attachment of the mesh to the sacrum or other apical structure, such as the sacrospinous ligament.

Figure 17:
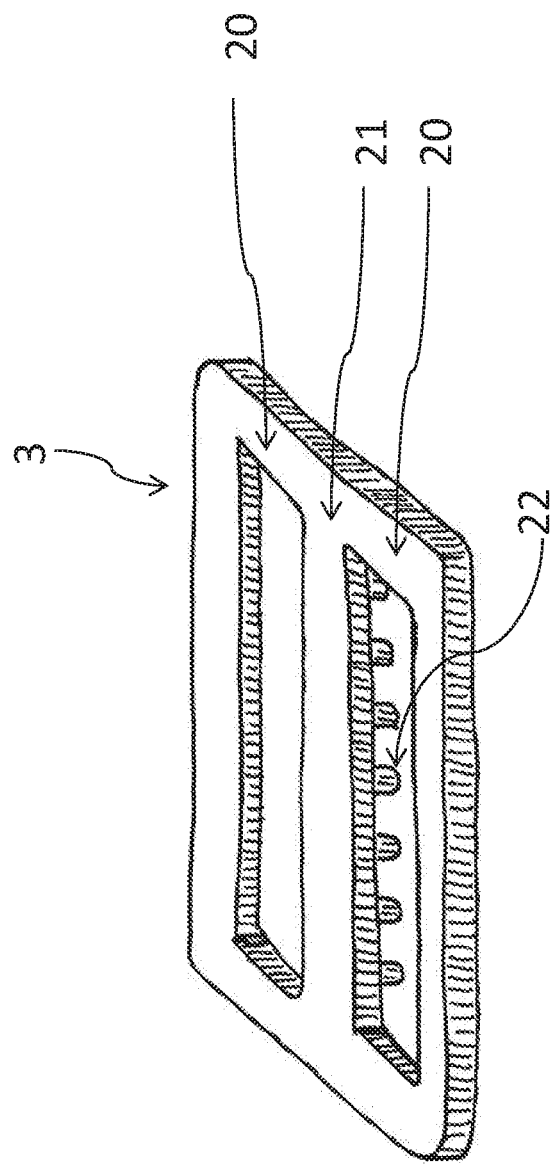
FIGS. 17-19 are schematic representations of exemplary embodiments of an eyelet which can be incorporated with the medical device, in accordance with the disclosed subject matter.

FIG. 17 depicts an exemplary embodiment of a grommet or eyelet (3) with a locking mechanism that prevents the mesh arm from backing out of the mesh body, after insertion through the eyelet. The needle with attached suture, plastic dilator and part of the mesh strip is inserted through the eyelet. The amount of the mesh strip that is inserted through the eyelet may be variable, as it is a function of the circumference of the cervix. The mechanism has a "back-pack"-like strap adjuster, in that there are a plurality (e.g. two illustrated) elongated slots (e.g. fenestrations) (20) through which the mesh cerclage (1) is placed, and in the base or central bar (21) between the fenestrations there are downwards-facing multiple stiff projections (22), in which the mesh cerclage gets caught, preventing slippage of the mesh cerclage.

Figure 18:
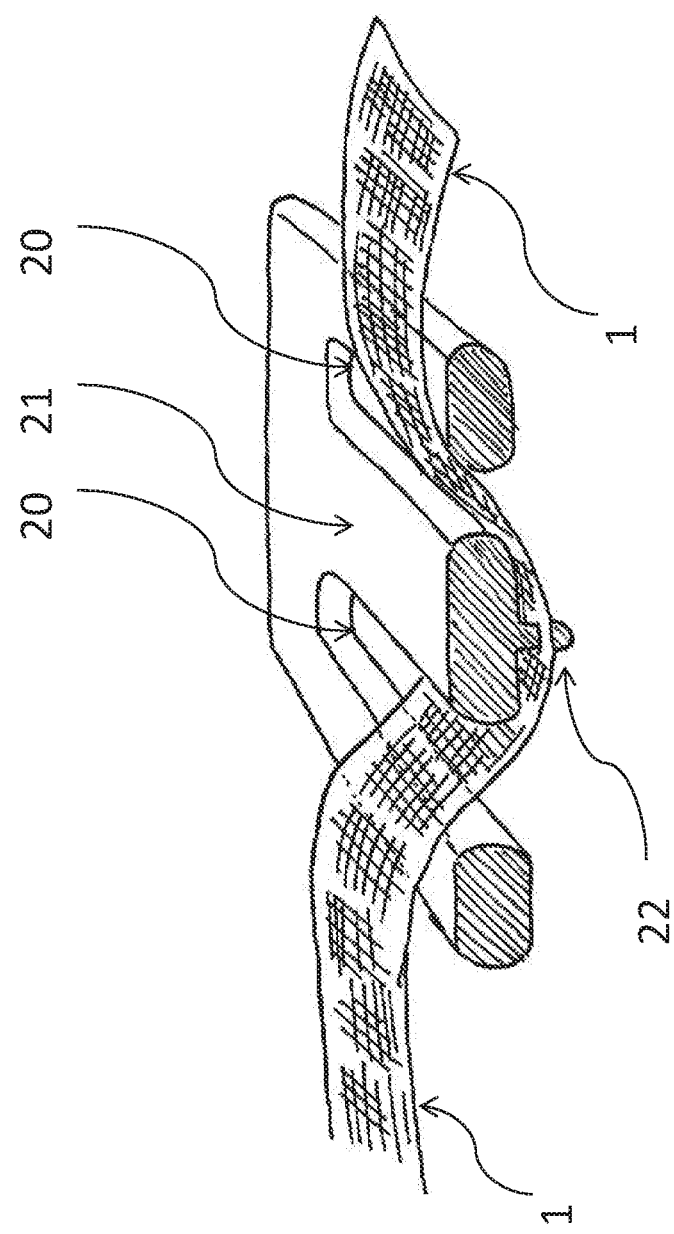

FIG. 18 depicts a cross-sectional view of the mechanism described in FIG. 17, with the "back-pack"-like strap adjuster, with the two elongated slots (e.g. fenestrations) (20), the central base bar (21) with the downwards-facing multiple stiff projections (22), in which the mesh cerclage (1) gets caught, preventing slippage of the mesh cerclage. The projections (22) are angled to permit insertion of the mesh, but will snag or engage the mesh (1) in the event a force is applied to attempt to remove the mesh from the slots (20).

Figure 19:
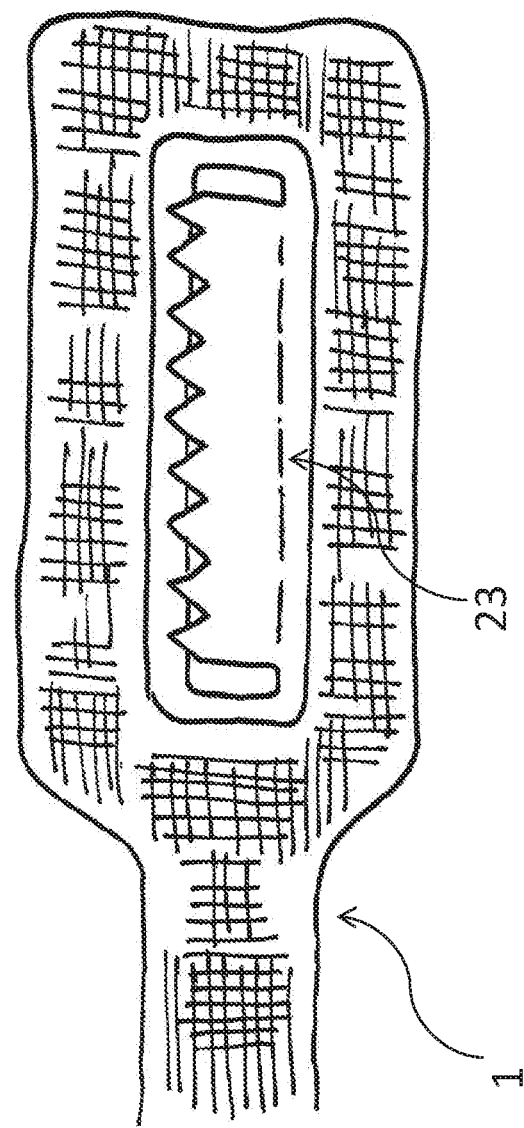

FIG. 19 depicts a mechanism on one end of the cerclage mesh strap (1) that has a slot (e.g. fenestration) (20), through which the other end of the mesh cerclage is inserted (after passing around the circumference of the cervix as a cerclage), and has a flap valve mechanism (23) with a jagged or "toothed" edge (24), in which the mesh cerclage material (1) is caught.

Figure 20:
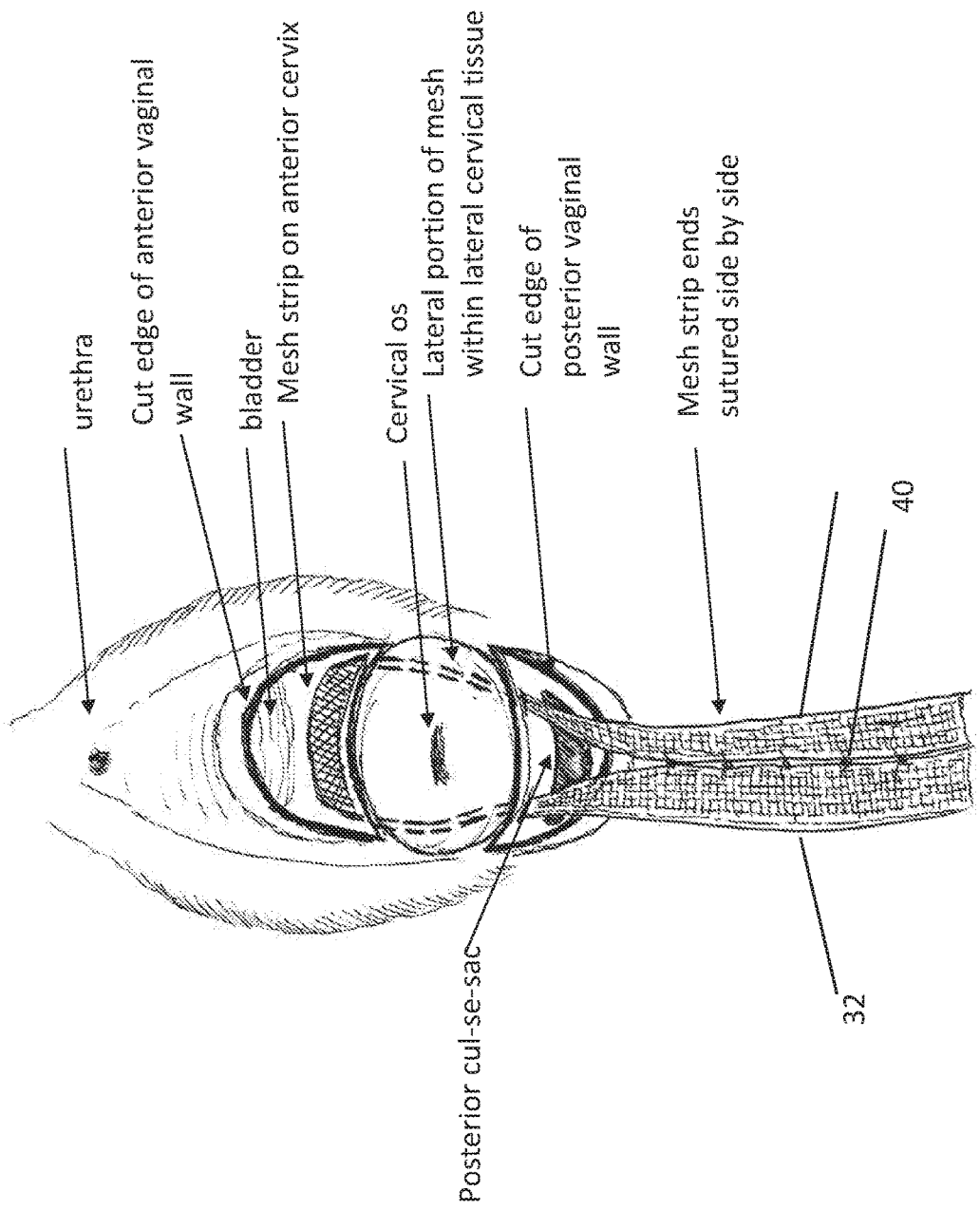
FIG. 20 is a schematic representation of an exemplary embodiment of the medical device with a plurality of mesh cerclage material arms coupled together, in accordance with the disclosed subject matter.
Figure 21:
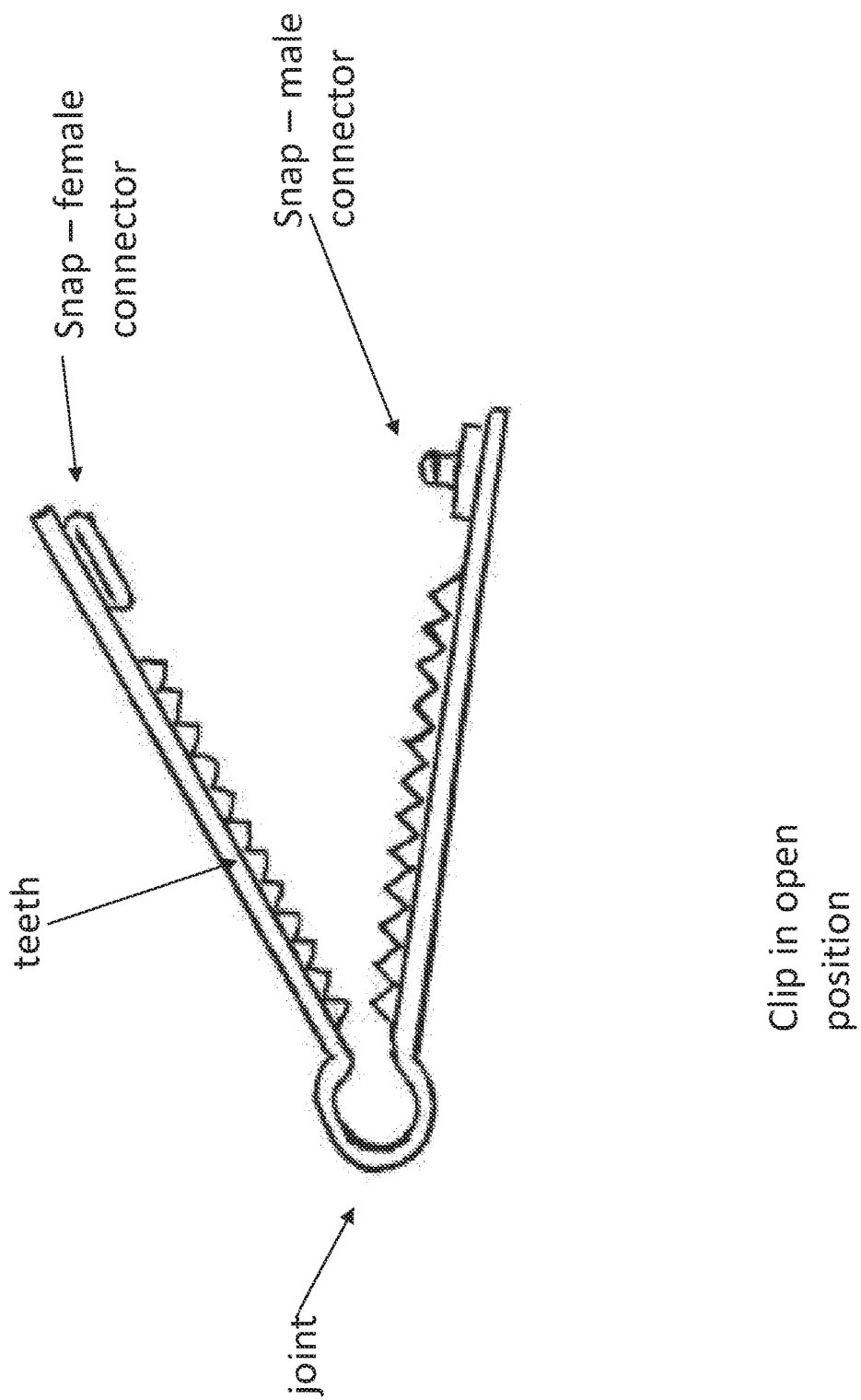
FIGS. 21-23 depict clip connectors suitable for affixing mesh to mesh.
Figure 22:
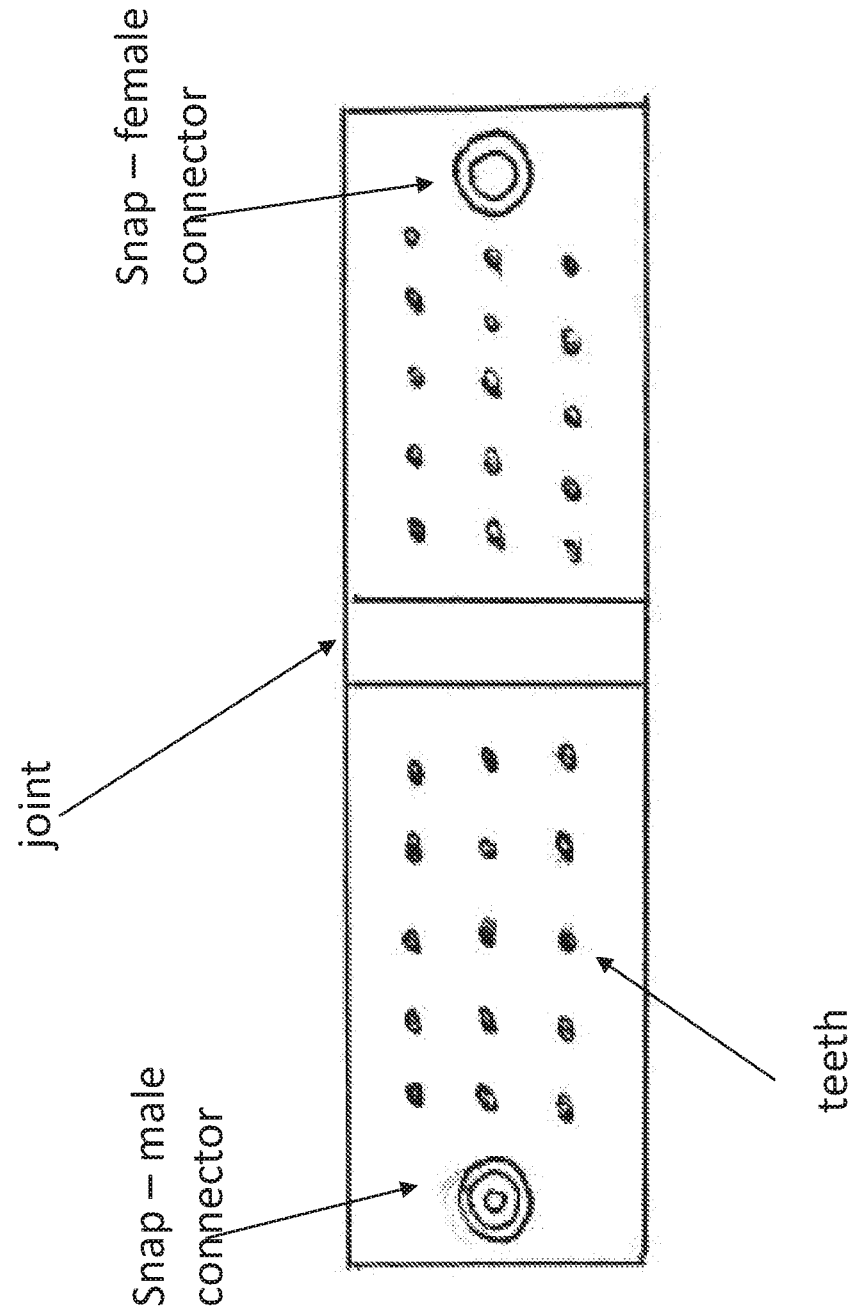
Figure 23:
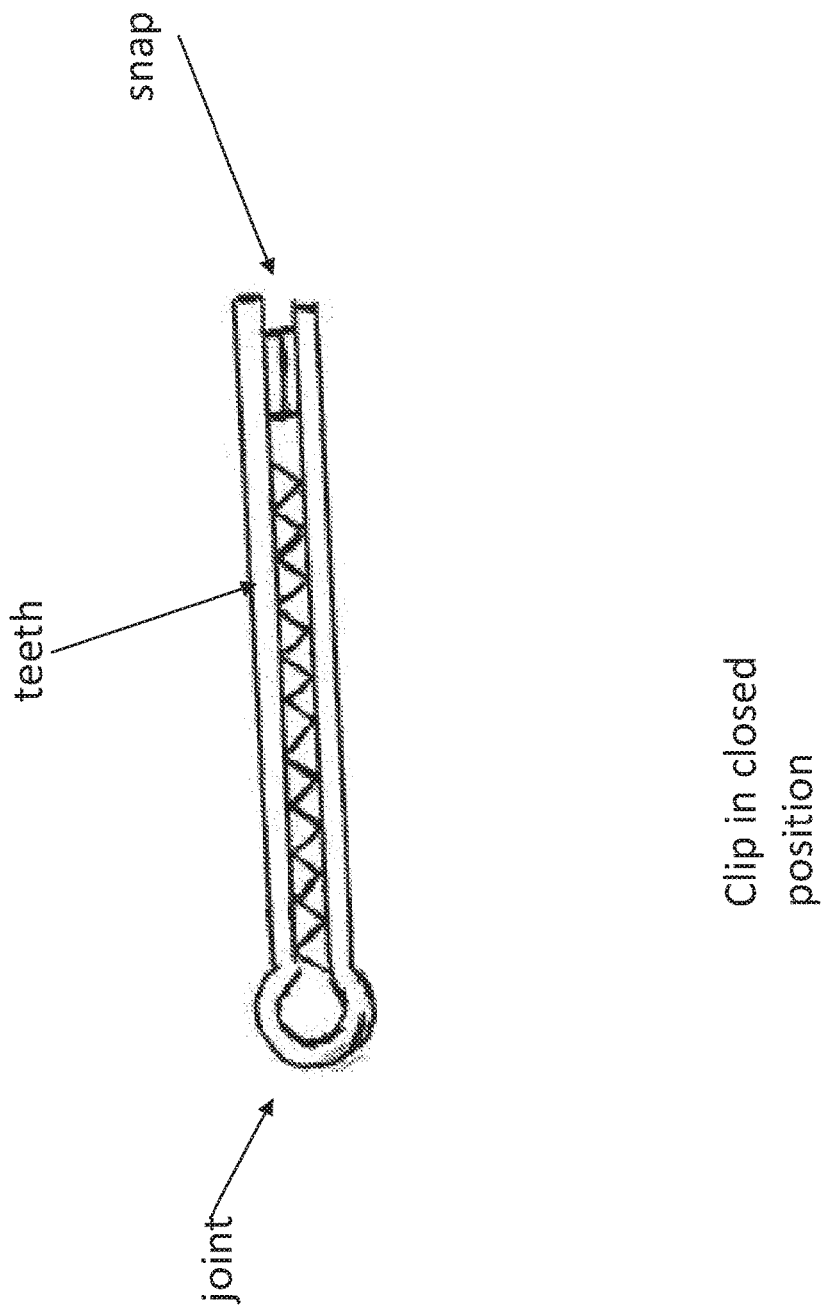

FIG. 20 depicts an exemplary embodiment of the medical device in which a central cerclage portion of an elongated mesh strip is used to form a cerclage around the cervix (e.g. at the cervical isthmus). The strip has a width extending from a first side to a laterally opposed second side. Thereafter the proximal and distal ends (30, 32) of the mesh, peripheral to the cerclage portion, are coupled together. The mesh ends (30, 32) are arranged adjacent to each other and coupled together by a variety of techniques, including stitching, clips (e.g. as shown in FIGS. 21-23), heat, glue, hook-and-loop fasteners, interrupted or continuous sutures, or other fastener(s) (40). The mesh ends may be coupled side-to-side, such that when they lie flat, they create a flat sacral portion having a width equal to the combined widths of the proximal and distal ends. The proximal and distal ends typically are joined first side to first side or second side to second side, though the first side of one end may be joined to the second side of the other end. This joining increases the size of the mesh available for sacral securement. The coupled mesh ends (30,32) are then attached to the sacrum. The mesh can be formed with a uniform width and thickness. Alternatively, the mesh can be formed with an increased width and/or thickness along the portion that forms the cerclage to locally increase the surface area and strength. The proximal and distal strip ends also may be coupled to another piece of mesh which is itself sacrally secured.

FIGS. 21-23 show three views of a clip-type connector. Two plates with gripping teeth are joined to one another by a hinge joint. A male snap and a female receptacle are disposed in complementary positions on the respective plates.

Figure 24:
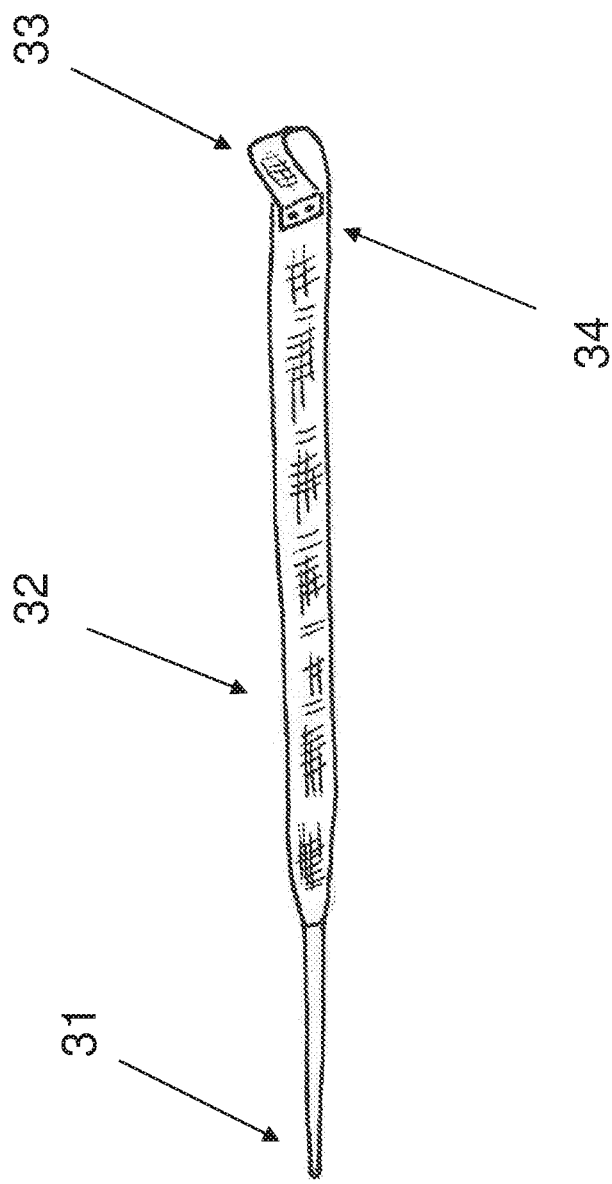
FIG. 24 illustrates an exemplary medical device in accordance with one or more embodiments having a needle attached to one end of a mesh strip with a loop at the other end, created by folding over the end of the mesh and fixating it to itself, with suture, ultrasonic welding, or some other method of attachment of mesh to mesh.

FIG. 24 illustrates an exemplary medical device in accordance with one or more embodiments having a needle (31) attached to one end of a mesh strip (32) with a folded over segment of the mesh in the other end of the mesh strip (33) with some form of fixation (34) to hold the mesh segment together, such as suture, ultrasonic welding or some other method of attachment of mesh to mesh.

Figure 25:
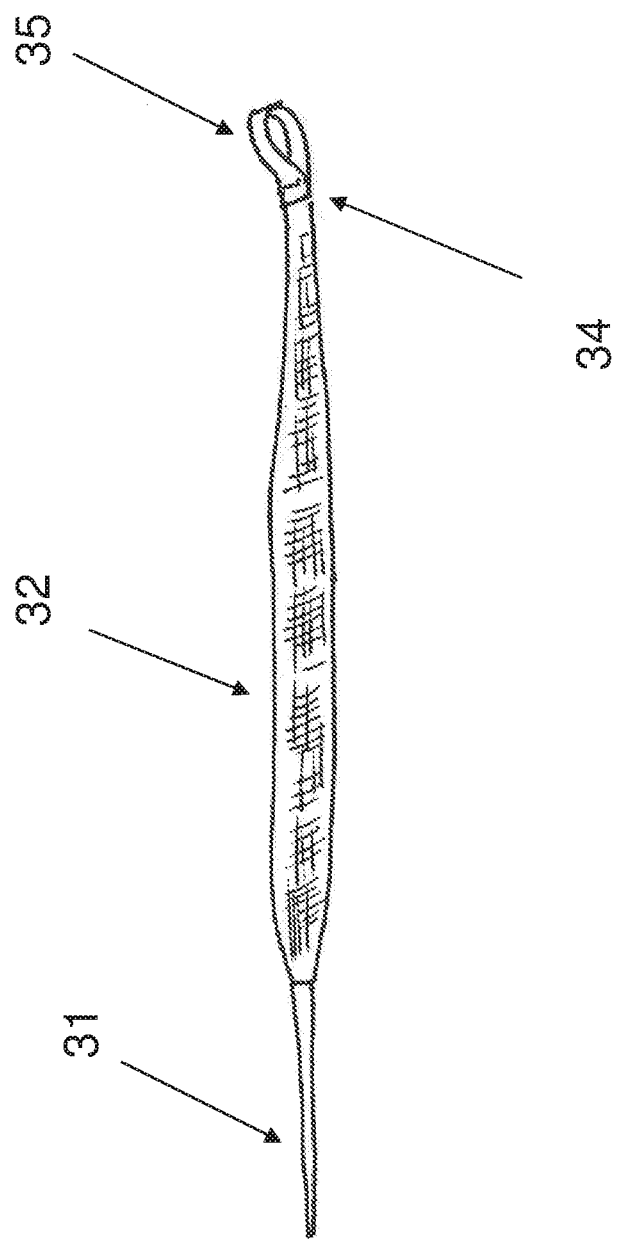
FIG. 25 illustrates an exemplary medical device in accordance with one or more embodiments having a needle attached to one end of a mesh strip with a more narrow loop at the other end, created by folding over a more narrow portion of the end of the mesh and fixating it to itself, with suture, ultrasonic welding, or some other method of attachment of mesh to mesh.

FIG. 25 illustrates an exemplary medical device in accordance with one or more embodiments having a needle (31) attached to one end of a mesh strip (32) with a narrower folded over segment of the mesh on the other end of the mesh strip (35) with some form of fixation (34) to hold the mesh segment together, such as suture, ultrasonic welding, or some other suitable method of attaching mesh to mesh.

Figure 26:
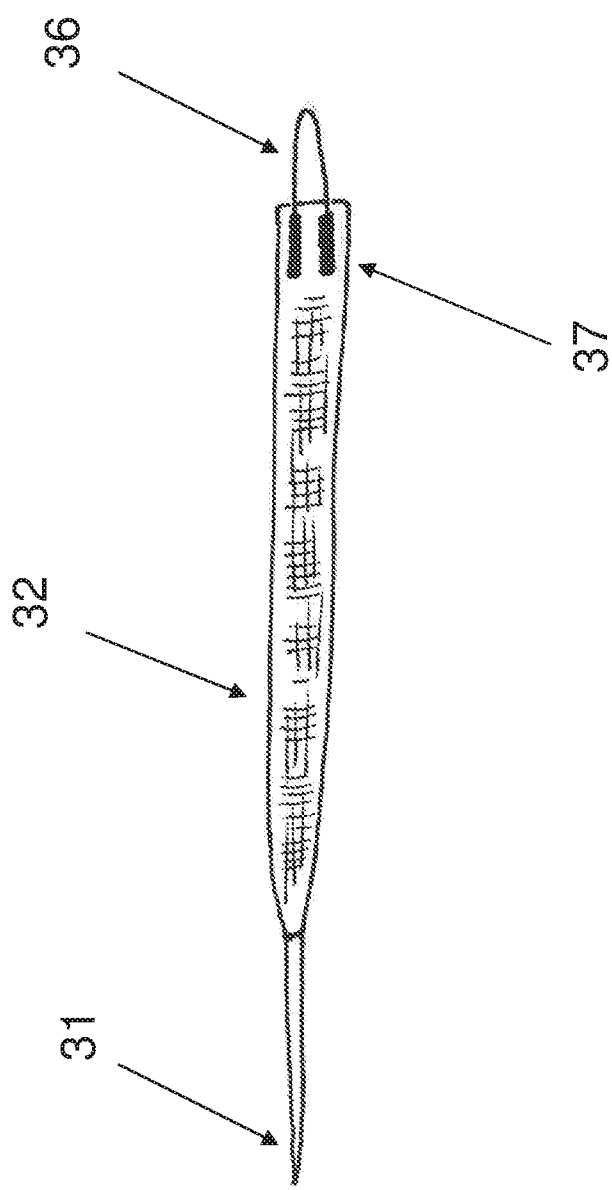
FIG. 26 illustrates an exemplary medical device in accordance with one or more embodiments having needle attached to one end of a mesh strip with a loop at the other end, created by a permanent suture attached to the end of the mesh. This may be a permanent suture material, such as polypropylene, and may be ultrasonically welded to the end of the mesh, or may be threaded through the end of the mesh and suture as a loop.

FIG. 26 illustrates an exemplary medical device in accordance with one or more embodiments having a needle (31) attached to one end of a mesh strip (32) with a loop at the other end (36), created by a permanent suture attached to the end of the mesh. This may be a permanent suture material, such as polypropylene, and may be ultrasonically welded to the end of the mesh (37), or may be threaded through the end of the mesh and suture as a loop.

Figure 27:
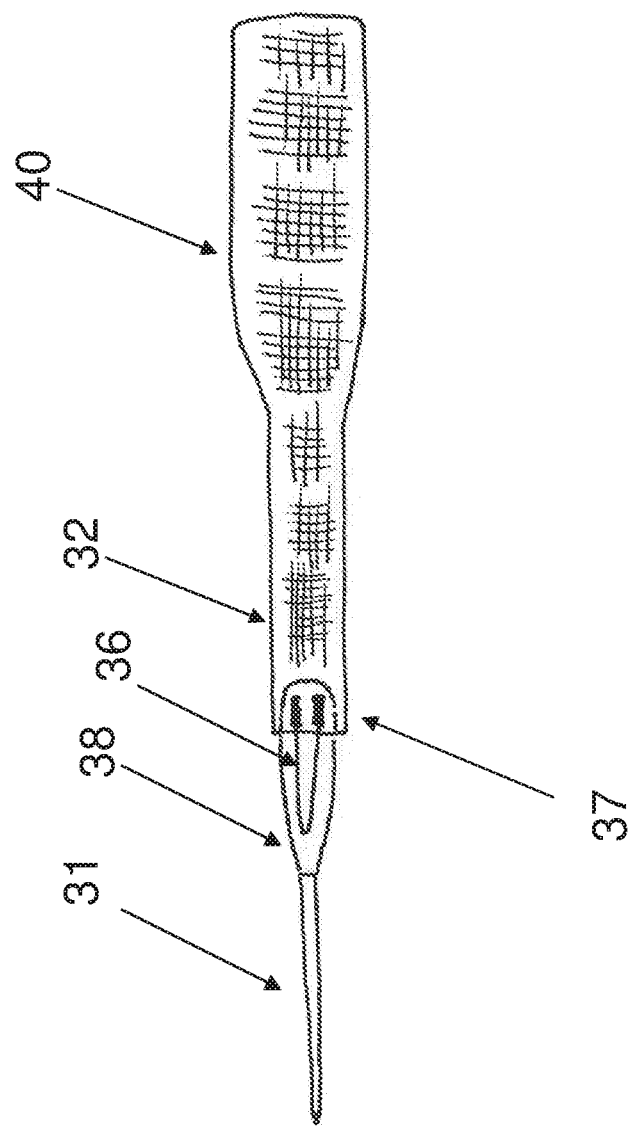
FIG. 27 illustrates an exemplary medical device in accordance with one or more embodiments having a needle swaged on to a loop of suture material, which is attached to the end of a mesh segment by either threading it through the mesh, ultrasonically welding it to the mesh, or some other mechanism of attachment. There is a second permanent suture loop on the same end of the mesh, which is also attached to the mesh by threading it through the mesh, ultrasonically welding it to the mesh, or some other mechanism of attachment. Once the cerclage is complete, the suture swaged on to the needle is cut, leaving the other loop attached, and the other end of the mesh strip is brought through the loop and then attached to the sacrum, after determining the proper tension.

FIG. 27 illustrates an exemplary medical device in accordance with one or more embodiments having a needle (31) swaged on to a loop of suture material (38), which is attached to the end of a mesh segment (32) by either threading it through the mesh, ultrasonically welding it to the mesh, or some other mechanism of attachment. There is a second permanent suture loop (36) on the same end of the mesh, which is also attached to the mesh by threading it through the mesh, ultrasonically welding it to the mesh (37), or some other mechanism of attachment. Once the cerclage is complete, the suture swaged on to the needle is cut, leaving the other loop attached, and the other end of the mesh strip, which may be wider than the end of the mesh with the suture loops attached (40), is brought through the loop and then attached to the sacrum, after determining the proper tension.

Figure 28:
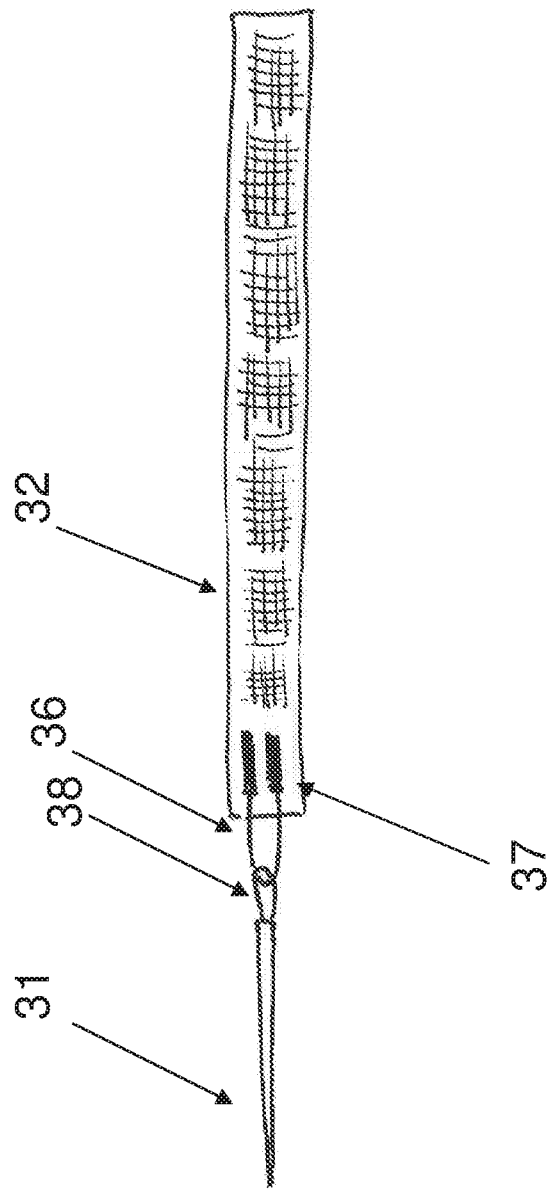
FIG. 28 illustrates an exemplary medical device in accordance with one or more embodiments having a needle swaged on to a suture loop, which is interlocked with another suture loop made of permanent suture, which is either threaded through, ultrasonically welded, or otherwise attached to the end of the mesh strip. Once the cerclage is complete, the suture swaged on to the needle is cut, leaving the other loop attached, and the other end of the mesh strip is brought through the loop and then attached to the sacrum, after determining the proper tension.

FIG. 28 illustrates an exemplary medical device in accordance with one or more embodiments having a needle (31) swaged on to a suture loop (38), which is interlocked with another suture loop made of permanent suture (36), which is either threaded through, ultrasonically welded (37), or otherwise attached to the end of the mesh strip (32). Once the cerclage is complete, the suture swaged on to the needle is cut, leaving the other loop attached, and the other end of the mesh strip is brought through the loop and then attached to the sacrum, after determining the proper tension.

Figure 29:
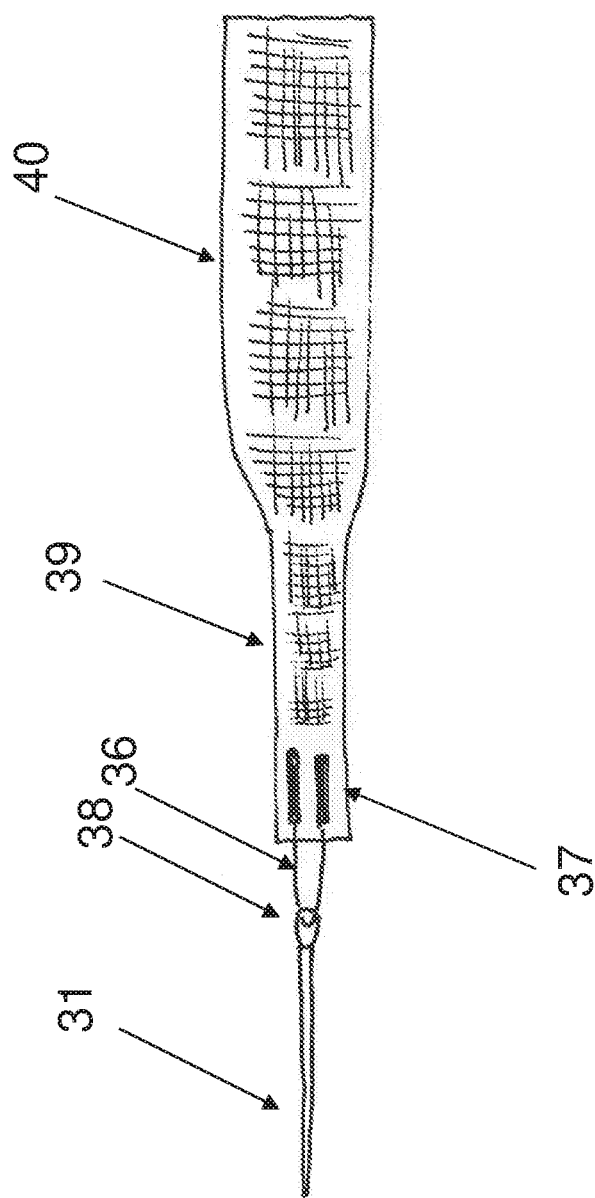
FIG. 29 illustrates an exemplary medical device in accordance with one or more embodiments having a needle swaged on to a suture loop, which is interlocked with another suture loop made of permanent suture, which is either threaded through, ultrasonically welded, or otherwise attached to the narrow end of the mesh strip, which may come in various lengths. The narrow mesh strip may then transition to a wider mesh strip for the remainder of the length of the mesh strip. Once the cerclage is complete, the suture swaged on to the needle is cut, leaving the other loop attached, and the wider end of the mesh strip is brought through the loop and then attached to the sacrum, after determining the proper tension.

FIG. 29 illustrates an exemplary medical device in accordance with one or more embodiments having a needle (31) swaged on to a suture loop (38), which is interlocked with another suture loop made of permanent suture (36), which is either threaded through, ultrasonically welded (37), or otherwise attached to the narrow segment of the mesh strip (39), which may come in various lengths. The narrow mesh strip may then transition to a wider mesh strip (40) for the remainder of the length of the mesh strip. Once the cerclage is complete, the suture swaged on to the needle is cut, leaving the other loop attached, and the wider end of the mesh strip is brought through the loop and then attached to the sacrum, after determining the proper tension.

Figure 30:
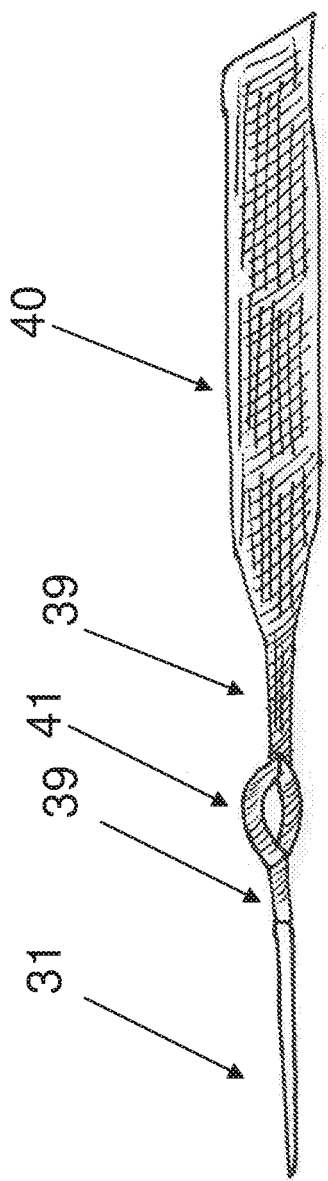
FIG. 30 illustrates an exemplary medical device in accordance with one or more embodiments having a needle swaged on to a narrow mesh strip, which is then attached to a loop of the mesh strip, which is then attached to another thin strip of mesh, which may come in various lengths. The narrow mesh strip may then transition to a wider mesh strip for the remainder of the length of the mesh strip. Once the cerclage is complete, the thin mesh strip swaged on to the needle is cut, leaving the mesh loop attached, and the wider end of the mesh strip is brought through the mesh loop and then attached to the sacrum, after determining the proper tension.

FIG. 30 illustrates an exemplary medical device in accordance with one or more embodiments having a needle (31) swaged on to a narrow mesh strip (39), which is then attached to a narrow loop of the mesh strip (41), which is then attached to another thin strip of mesh (39), which may come in various lengths. The narrow mesh strip may then transition to a wider mesh strip (40) for the remainder of the length of the mesh strip. Once the cerclage is complete, the thin mesh strip swaged on to the needle is cut, leaving the mesh loop attached, and the wider end of the mesh strip is brought through the mesh loop and then attached to the sacrum, after determining the proper tension.

Figure 31:
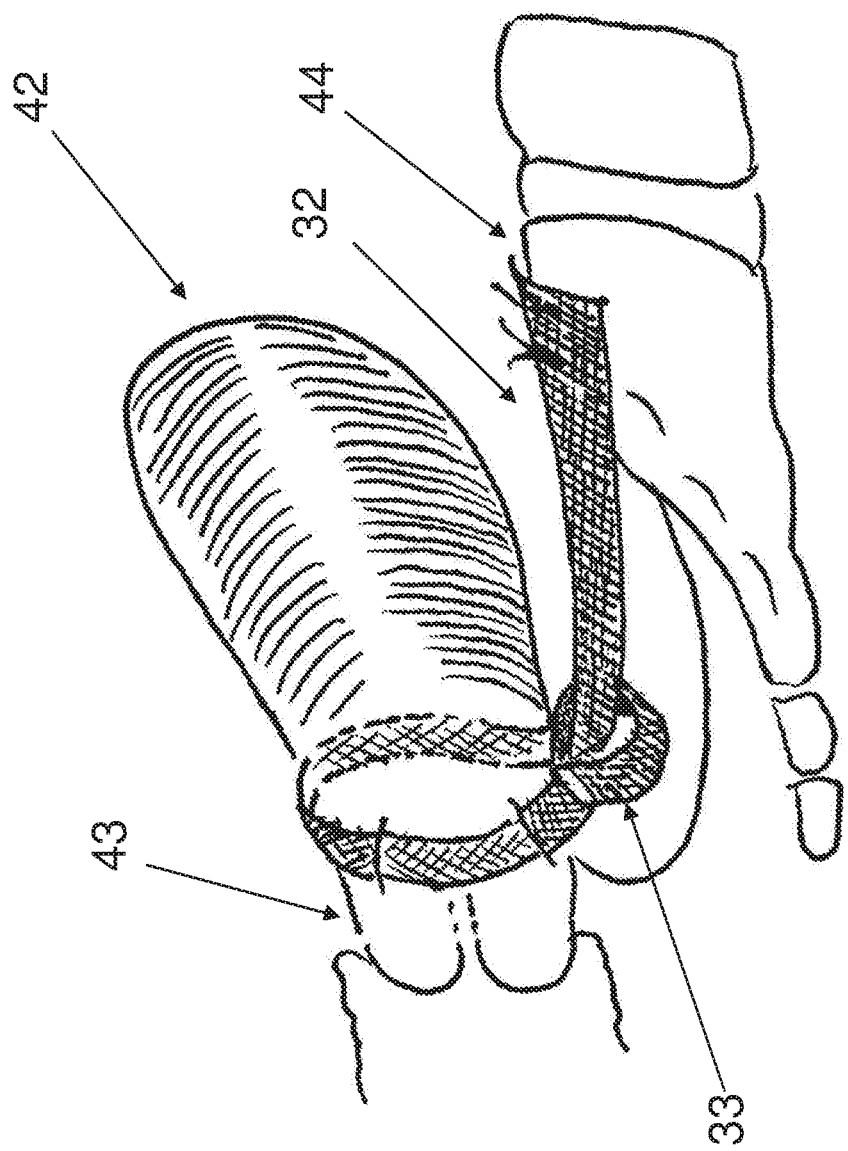
FIG. 31 demonstrates the position of an exemplary device in accordance with one or more embodiments after placement around the cervix as a cerclage with one end of the mesh strip having a loop on the end, and the other end of the mesh strip passing through the loop and then attached to the sacral promontory.

FIG. 31 demonstrates a sagittal view of the pelvis with an exemplary device in accordance with one or more embodiments in place around the cervix (43), near the junction with the uterus (42). After placement of the mesh strip (32) of the device around the cervix, the loop in the mesh (33) remains posterior to the cervix and the other end of the mesh strip (32) passes through the loop and is attached to the sacral promontory (44).

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed. As noted above, reference to "mesh" is to be taken as a reference to other flat, flexible materials in the alternative or in combination.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An implantable cerclage sacrocolpopexy medical device, comprising:
   an elongate strip of flat, flexible material extending longitudinally from a first end to an opposite second end;
   a surgical needle attached to the first end of the elongate strip; and
   a loop at either:
   (1) the first end of the elongate strip proximate the needle, wherein the loop is sized and shaped to enable passage therethrough of the second end of the elongate strip after the elongate strip has been positioned to encircle the cervix in a cerclage configuration and the needle has been detached from the elongate strip, and wherein the second end of the elongate strip is configured for attachment to the sacrum or sacrospinous ligament, or
   (2) the second end of the elongate strip, wherein the loop is sized and shaped to enable passage therethrough of the first end of the elongate strip after the elongate strip has been positioned to encircle the cervix in a cerclage configuration and the needle has been detached from the elongate strip, and wherein the first end of the elongate strip is configured for attachment to the sacrum or sacrospinous ligament.

2. The medical device of claim 1, wherein the flat, flexible material comprises a mesh material.

3. The medical device of claim 1, wherein the flat, flexible material comprises a fabric or a non-cross-linked biologic graft.

4. The medical device of claim 1, wherein the needle is either straight or curved, and either sharp or blunt-tipped.

5. The medical device of claim 1, wherein the surgical needle is swaged to the first end of the elongate strip.

6. The medical device of claim 5, further comprising a sleeve covering an area of the device where the needle is swaged to the first end of the elongate strip to reduce resistance when the device is moved through cervical tissue.

7. The medical device of claim 1, wherein the loop is formed from a portion of the elongate strip folded over and affixed to itself.

8. The medical device of claim 7, wherein the portion of the elongate strip is affixed to itself using suturing or ultrasonic welding.

9. The medical device of claim 1, wherein the elongate strip is tapered proximate the loop.

10. The medical device of claim 1, wherein the surgical needle is swaged onto a suture loop attached to the first end of the elongate strip.

11. The medical device of claim 1, wherein the loop is at the second end of the elongate strip, and wherein the loop is formed from a suture attached to the second end of the elongate strip.

12. The medical device of claim 1, wherein the loop is at the first end of the elongate strip, and wherein the loop is formed from a suture attached to the first end of the elongate strip.

13. The medical device of claim 12, wherein the surgical needle is attached to the first end of the elongate strip using another suture.

14. The medical device of claim 12, wherein the surgical needle is attached to the loop using another suture forming another loop interlocked with the loop.

15. The medical device of claim 12, wherein the second end of the elongate strip is wider than the first end of the elongate strip.

16. A method of treating prolapse in a patient, comprising:
   (a) positioning an implantable cerclage sacrocolpopexy medical device circumferentially around the cervix of the patient, said medical device comprising an elongate strip of flat, flexible material extending longitudinally from a first end to an opposite second end, a surgical needle attached to the first end of the elongate strip, and a loop at either the first end or the second end;
   (b) detaching the surgical needle from the medical device and removing the surgical needle from the operative field;
   (c) passing the end of the elongate strip opposite the end having the loop through the loop; and
   (d) attaching the end of the elongate strip passed through the loop to the sacrum or sacrospinous ligament of the patient.

17. The method of claim 16, further comprising applying a suitable tension in the elongate strip prior to step (d).

18. The method of claim 16, wherein step (d) comprises suturing the elongate strip or applying surgical tacks to the elongate strip.

* * * * *